(12) United States Patent
Nasrallah et al.

(10) Patent No.: US 11,694,774 B9
(48) Date of Correction: Jun. 17, 2025

CORRECTED PATENT

(54) PLATFORM FOR PERPETUAL CLINICAL COLLABORATION AND INNOVATION WITH PATIENT COMMUNICATION USING ANONYMIZED ELECTRONIC HEALTH RECORD DATA, CLINICAL, AND PATIENT REPORTED OUTCOMES AND DATA

(71) Applicant: Avident Health, LLC, Baltimore, MD (US)

(72) Inventors: Walid Fawzi Nasrallah, Austin, TX (US); Tan Lu, Owings Mills, MD (US)

(73) Assignee: AVIDENT HEALTH, LLC, Baltimore, MD (US)

(*) Notice: Subject to any disclaimer, the term of this patent is extended or adjusted under 35 U.S.C. 154(b) by 679 days.

(21) Appl. No.: 16/598,793

(22) Filed: Oct. 10, 2019

(45) Date of Patent: Jul. 4, 2023

(15) Correction Data

US 11,694,774 B1 with issue date Jul. 4, 2023, incorrectly issued as US 12,345,678 B1 with issue date May 22, 2022.
See (10), (45), and term adjustment in the Notice, and drawings.

Related U.S. Application Data

(60) Provisional application No. 62/744,051, filed on Oct. 10, 2018.

(51) Int. Cl.
*G16H 10/60* (2018.01)
*G06N 5/04* (2023.01)
*G06N 20/00* (2019.01)

(52) U.S. Cl.
CPC .............. *G16H 10/60* (2018.01); *G06N 5/04* (2013.01); *G06N 20/00* (2019.01)

(58) Field of Classification Search
CPC ........... G16H 10/60; G06N 5/04; G06N 20/00
See application file for complete search history.

(56) References Cited

U.S. PATENT DOCUMENTS

| 9,582,838 | B1 | 2/2017 | Henderson et al. | |
| 2001/0034615 | A1* | 10/2001 | Wilkinson et al. | .... G16H 80/00 705/2 |

(Continued)

OTHER PUBLICATIONS

U.S. Appl. No. 14/640,975 Office Action dated Mar. 5, 2019.

(Continued)

*Primary Examiner* — Jonathan Ng
*Assistant Examiner* — Benjamin L. Hanks
(74) *Attorney, Agent, or Firm* — Wilson Sonsini Goodrich & Rosati

(57) ABSTRACT

Described are web-based clinical data stores; mobile clinician applications, web-based patient portals, and aggregated decision engines comprising: a translation module configured to express aggregated electronic medical records in a format that is human-readable and accessible to an inference engine and/ or a machine learning algorithm; a notation module configured to express relationships between treatment steps to generate human-readable diagrams and to transmit the diagrams as instructions to the inference engine or the machine learning algorithm; an encryption-based decentralized zero-trust de-identification and anonymization module to protect private patient information when releasing records for research purposes outside the treating physician's protected network; an inference engine configured to receive inputs from the translated medical records of a patient and a subset of interlinked treatment steps selected by the treating physician to generate outputs comprising predictions and probabilities; and a machine learning algorithm configured to read and aggregate the anonymized; translated medical records of multiple patients from multiple treating physicians and possibly combine them with one or more tumor registries to test hypotheses.

24 Claims, 28 Drawing Sheets

(56) References Cited

U.S. PATENT DOCUMENTS

| | | | |
|---|---|---|---|
| 2003/0110059 A1 | 6/2003 | Janas et al. | |
| 2006/0031094 A1 | 2/2006 | Cohen et al. | |
| 2006/0235280 A1 | 10/2006 | Vonk et al. | |
| 2008/0281639 A1 | 11/2008 | Quinn et al. | |
| 2009/0119282 A1 | 5/2009 | Load et al. | |
| 2011/0208540 A1 | 8/2011 | Lord et al. | |
| 2011/0301977 A1* | 12/2011 | Belcher et al. | G16H 10/60 715/764 |
| 2012/0066000 A1 | 3/2012 | Opfer et al. | |
| 2012/0101847 A1 | 4/2012 | Johnson et al. | |
| 2012/0231959 A1 | 9/2012 | Elton et al. | |
| 2013/0110547 A1* | 5/2013 | Englund et al. | G16H 10/60 705/3 |
| 2013/0166317 A1 | 6/2013 | Beardall et al. | |
| 2013/0226617 A1 | 8/2013 | Mok et al. | |
| 2013/0317844 A1 | 11/2013 | Hammond et al. | |
| 2014/0058742 A1 | 2/2014 | Chari et al. | |
| 2014/0108024 A1 | 4/2014 | Evans et al. | |
| 2014/0249851 A1 | 9/2014 | Christodouleas et al. | |
| 2014/0316821 A1 | 10/2014 | Sheffield et al. | |
| 2016/0012189 A1* | 1/2016 | Farha et al. | G16H 70/20 705/2 |
| 2018/0018590 A1* | 1/2018 | Szeto et al. | G06N 20/10 |

OTHER PUBLICATIONS

U.S. Appl. No. 14/640,975 Office Action dated Nov. 30, 2017.
U.S. Appl. No. 14/640,975 Office Action dated Jun. 16, 2020.
U.S. Appl. No. 14/640,975 Office Action dated Mar. 30, 2021.

* cited by examiner

Fig. 3

Enter Your Verification Code?

Request new code in 51 seconds

Login to Different Account

Fig. 4
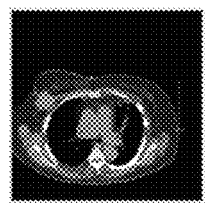
71 YO with Stag...
71 YO with a 5 cm hard mass attached to the skin and the pectoralis major in the right b...
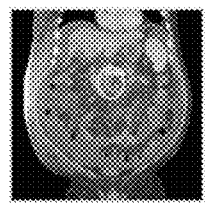
Are you coming...
Follow link to answer question
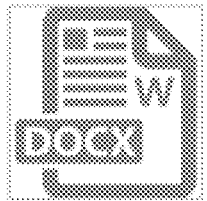
EMRs Decried b... NEW
Death By A Thousand Clicks: Leading Boston Doctors Decry Electronic Medical Records...

Fig. 6

7 comments from 4 people:

Boz Borowiecki  2018-5-15
@Aleka Farha – and you can send messages to specific Co-Collaborators, by using the "@" function

Maen Farha  2018-5-7

Boz Borowiecki  2018-5-7
That's a lot of money! Will it affect the treatment decisions?

Maen Farha  2018-5-7
The local disease can become problematic very quickly!!

Maen Farha  2018-5-7
The patient has slow er pos disease with few small mets. She will likely have a meaningful chance at long term survival.

Fig. 7
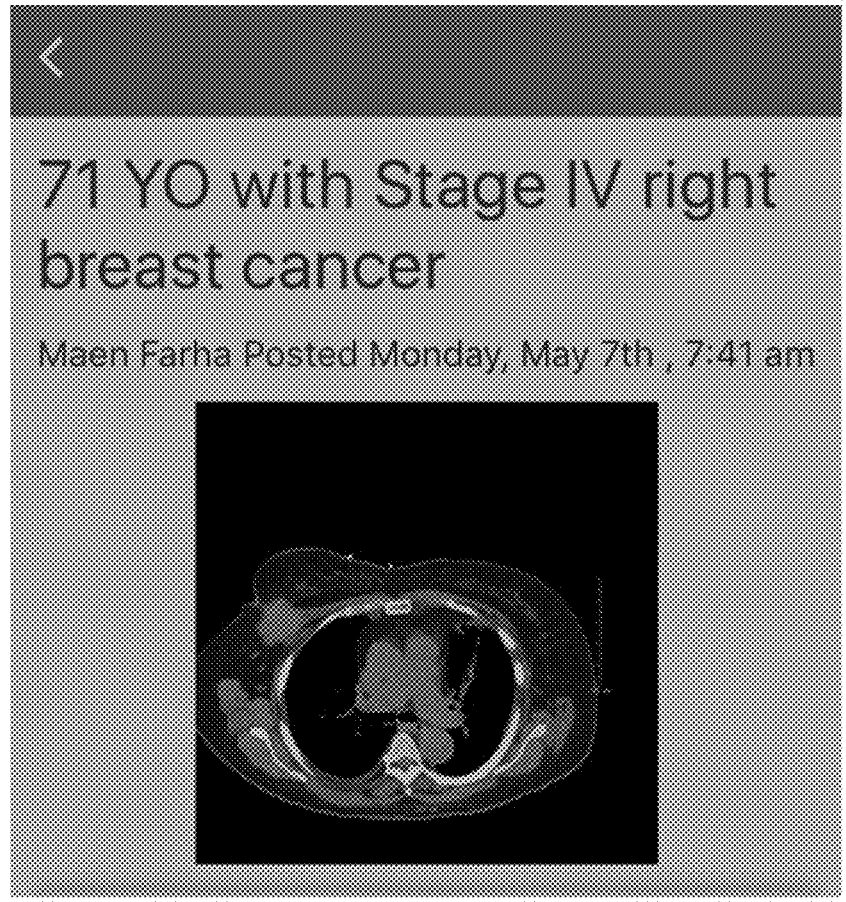
Click to Record
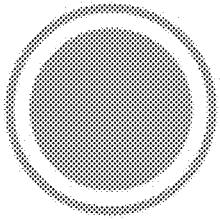
cancel

PLATFORM FOR PERPETUAL CLINICAL COLLABORATION AND INNOVATION WITH PATIENT COMMUNICATION USING ANONYMIZED ELECTRONIC HEALTH RECORD DATA, CLINICAL, AND PATIENT REPORTED OUTCOMES AND DATA

CROSS-REFERENCE TO RELATED APPLICATIONS

This application claims the benefit of U.S. Application Ser. No. 62/744,051, filed Oct. 10, 2018, which is hereby incorporated by reference in its entirety.

BACKGROUND

The American Cancer Society reports 1,685,210 new cancer cases with 595,690 deaths in the USA in 2016. Female breast cancer accounts to 246,660 new cases. The medical cost of cancer care continues to climb at a fast rate and presents a large financial burden. The medical cost of cancer care is expected to climb to $158 billion in 2020.

SUMMARY OF THE INVENTION

The National Academy of Medicine, in its 2013 STUDY: Delivering High-Quality Cancer Care: Charting a New Course for a System in Crisis, identified three factors that impact negatively on the outcomes of cancer care: 1) The fragmented nature of care that causes poor collaboration among the cancer care teams; 2) Poor patient engagement and education leading to anxiety, poor compliance, and suboptimal decision-making; and 3) An estimated 30% of the $150 billion spent on cancer care annually is wasted on overtreatment and unnecessary procedures. In oncology practice, it is not uncommon for patients and families to complain about poor communication and engagement. Similar problems are encountered in the management of most interdisciplinary illnesses covering a wide range of diseases, specialties and hospital functions, including, but not limited to: ICU management, cardiology, patient admission, and emergency room communication.

The current tools available, which include multidisciplinary tumor conferences, multidisciplinary clinics, electronic health records (EHRs), patient portals, tumor registries, and virtual or video-conference tumor boards fail to address these, and other, concerns and fail to create the teamworking and engagement needed from users. multidisciplinary tumor conferences provide evidence of the value of the multidisciplinary care process to improve care and may have a positive influence on survival. However, they meet weekly at most and a patient may fall out of discussion for several weeks, or may often be discussed without the presence of their whole team. Multidisciplinary clinics have shown their effectiveness in encouraging involvement of patients and their families, reducing patient anxiety and the time from diagnosis to treatment. That said, the time requirement and preparation are substantial, and the discussion and patient involvement decrease markedly after the face-to-face encounter. These time requirements have led to very rare adoption of that model. EHRs provide a minimal degree of collaboration and are choked by the amount of "data" collected, largely to justify billing level and provide legal protection. Moreover, EHRs copy the paper record in their structure making structured data hard to find, retrieve, and analyze. Highlights from a review article on the role of EHRs in collaboration noted: "EHR improved documentation efficiency but also increased work routine variability. EHR increased cognitive load due to information fragmentation making retrieval more difficult. EHR's data storage and retrieval focus limited its effectiveness in supporting collaboration." Patient portals have failed so far to deliver on their promise of collaboration and patient involvement and education. They act mainly as a means to share results and patients find them crowded and confusing, not a real collaboration environment. In reality Athena Health reports an adoption rate from 10-35% depending on patients' age group. Virtual tumor boards are finally coming into the picture. However, they do not involve patients and will probably be loaded with "data" that does not drive decision making and are not mobile.

Described herein are platforms, systems, non-transitory computer readable media, methods comprising: a server processor configured to provide a web-based data store comprising: a software module interfacing with a plurality of electronic medical records; and a structured data store comprising a plurality of patient profiles, each patient profile comprising aggregated electronic medical records; a mobile processor configured to provide a mobile clinician application comprising: a software module presenting a group management interface allowing a project lead to define and edit a clinical project comprising: a patient profile and a plurality of clinicians including a treating physician; a software module providing an interdisciplinary collaboration environment comprising: a messaging service, a document sharing service, a list of performed and upcoming clinical procedures, and a notification service for the plurality of clinicians and pertaining to the clinical project; and a software module performing clinician engagement analytics; a server processor configured to provide a web-based patient portal comprising a software module providing a patient help center comprising: a messaging service, a list of performed and upcoming clinical procedures, and a notification service for the patient and pertaining to the clinical project; and a server processor configured to provide an aggregated relevant decision driving engine comprising: a translation module configured to express the aggregated electronic medical records in a format that is human-readable and accessible to a native inference engine, a supervised machine learning algorithm, or both; a notation module configured to express relationships between treatment steps to generate human-readable and human-editable node-and-arc diagrams and to transmit the diagrams as readable instructions to the native inference engine or the supervised machine learning algorithm; an anonymization module configured to maintain the separation between patient treatment or demographic records and private patient information revealing the identity of individual patients or of their treating physician, without implicitly or explicitly relying on trust in any party that may be subject to attack by a malicious actor seeking such access; a native inference engine configured to receive inputs from the translated medical records of a patient and a subset of interlinked treatment steps selected by the treating physician to generate outputs comprising predictions and probabilities; and a supervised machine learning algorithm configured to read and aggregate the translated medical records of multiple patients and combine them with one or more tumor registries to test hypotheses about the efficacy of potential courses of treatment for particular subsets pf patients. In some embodiments, one or more of the inference engine inputs are parsed from the translated medical records and comprise a provider decision or a patient behavior. In some embodiments, one or more of the inference engine outputs comprise a result of a diagnostic procedure or the patient's response to a treatment. In some embodiments, the clinical project comprises diagnosis and treatment of disease. In further embodiments, the disease comprises cancer. In still further embodiments, the cancer comprises breast cancer. In some embodiments, the platform further comprises a distributed zero-trust-architecture ledger system configured to apply selective anonymization, encryption, authentication, and inalterable electronic tagging of incoming and outgoing data based on permissions assigned to a party requesting to read or write data, by using permissioned Blockchain, Merkle Tree, or other public-private key encryption models, including Quantum-based encryption schemes. In some embodiments, the distributed ledger system is used to plan, initiate, conduct, track, or report a clinical trial in an accelerated fashion. In some embodiments, the party requesting to read or write data is a medical researcher testing one or more hypotheses about patient treatment. In other embodiments, the party requesting to read or write data is a medical practitioner seeking latest available data about the efficacy of a certain treatment for an existing patient. In yet other embodiments, the party requesting to read or write data is a patient or patient-authorized agent seeking detailed understanding of past treatment steps, or past or present descriptions of the patient's condition, or potential future treatment steps and probabilities associated with the different outcomes of each treatment option, including any physician's comments on any of the above. In some embodiments, the native inference engine is programmed to notify one or more of the plurality of clinicians to one or more clinical trials relevant to the patient using the notification service of the interdisciplinary collaboration environment. In a particular embodiment, the mobile clinician application is a native mobile application. In some embodiments, the messaging service of the interdisciplinary collaboration environment allows a clinician to send and receive text messages, voice messages, photo messages, video messages, or any combination thereof. In some embodiments, the messaging service of the interdisciplinary collaboration environment allows a clinician to send a message to: the patient, the plurality of clinicians, or a subset of the plurality of clinicians. In some embodiments, the messaging service of the interdisciplinary collaboration environment allows a clinician to poll the plurality of clinicians or a subset of the plurality of clinicians. In various embodiments, the notification service of the interdisciplinary collaboration environment utilizes SMS, push notification, email, voice mail, or any combination thereof. In some embodiments, the document sharing service of the interdisciplinary collaboration environment allows sharing of lab results, pathology reports, medical images, radiology reports, surgical reports, or any combination thereof. In some embodiments, the messaging service of the patient help center allows the patient to send and receive text messages, voice messages, photo messages, video messages, or any combination thereof. In some embodiments, the messaging service of the patient help center allows the patient to send a message to: the plurality of clinicians or a subset of the plurality of clinicians. In various embodiments, the notification service of the patient help center utilizes SMS, push notification, email, voice mail, or any combination thereof. In some embodiments, the platform further comprises a server processor configured to provide a clinical analytics system comprising a software module checking the performed and upcoming clinical procedures against a predetermined standard and generating a notification if any procedure is outside the standard. In some embodiments, the platform further comprises a server processor configured to provide a web-based administrative dashboard application comprising a software module generating a suite of administrative reports. In further embodiments, the suite of administrative reports comprises one or more of: a quality of patient care report, a cost of patient care report, a patient profile report, an upcoming procedure report, a rate of guideline compliance report, and a clinician engagement report.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 is a non-limiting example of a graphic user interface (GUI), in this case, a mobile clinician application GUI including features for account creation and log in;

FIG. 3 is a non-limiting example of a graphic user interface, in this case, a mobile clinician application GUI including features for two-factor account authentication;

FIG. 4 is a non-limiting example of a graphic user interface, in this case, a mobile clinician application GUI including an interdisciplinary collaboration environment with features for accessing a plurality of clinical projects;

FIG. 6 is a non-limiting example of a graphic user interface, in this case, a mobile clinician application GUI including an interdisciplinary collaboration environment with features for participating in a discussion for a particular clinical project;

FIG. 7 is a non-limiting example of a graphic user interface, in this case, a mobile clinician application GUI including an interdisciplinary collaboration environment with features for recording a voice message for a particular clinical project;

DETAILED DESCRIPTION OF THE INVENTION

Certain Definitions

Figure 1:
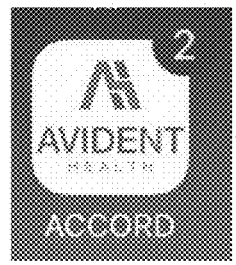
FIG. 1 is a non-limiting example of an application icon, in this case, an application icon displaying a notification badge.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

As used herein, "de-identification" means removing a person's identity from a record.

As used herein, "anonymization" means removing all, or substantially all, clues that could, through statistical analysis, permit an unauthorized "attacker" from inferring the identity of the owner of a de-identified record.

Overview: Accord by Avident Health is a mobile application, integrated with other components, built to improve collaboration among health care providers, hospital administrators, and patients as well. Inefficient communication tools used today and time and space constraints lead to inefficiency, errors and waste. In some embodiments, Avident Health Accord app provides a HIPAA compliant, multi-use collaboration environment for different treatment team members and patients to communicate efficiently around patient care decisions. Practical use cases include, for example, virtual discussions of patient cases, analysis and decision making for new technologies, and information and discussion about clinical trials. In various embodiments, components of Accord include:

An online collaboration space where a project lead can initiate a discussion on a wide-ranging set of topics creating a project team and a unified set of relevant information;

A chat message board for administrators, nurses, doctors and eventually patients can leave text, voice, and photo messages to each other;

An alert system leveraging push notifications and SMS text messaging to allow asynchronous chat-based collaboration;

A secure space to store and share documents;

An analytic system tracking participant engagement and feedback; and/or An app that is HIPAA-compliant insuring patient confidentiality and the safety of PHI.

Data Store

In some embodiments, the platforms, systems, media, and methods described herein include a data store. In further embodiments, the data store is implemented as a web-based or cloud-based database. The data store suitably includes many types of data including, by way of non-limiting example, electronic medical records and their contents such as patent demographic information, patient histories, diagnostic information, medical test results, therapeutic information, clinician notes, medical imaging data, and the like. In some embodiments, the data store is a structured data store allowing data originating from disparate sources to be compared across records, patients, organizations, and the like.

Clinician Application

In some embodiments, the platforms, systems, media, and methods described herein include a clinician application. In various embodiments, the clinician application is a web application, a stand-alone application, and/or a mobile application. Preferably, the clinician application is a mobile application to facilitate convenient and frequent use by busy clinicians. In some embodiments, the clinician application includes a software module presenting a group management interface allowing a project lead to define and edit a clinical project comprising: a patient profile and a plurality of clinicians including a treating physician. In some embodiments, the clinician application includes a software module providing an interdisciplinary collaboration environment comprising: a messaging service, a document sharing service, a list of performed and upcoming clinical procedures, and a notification service for the plurality of clinicians and pertaining to the clinical project. In some embodiments, the clinician application includes a software module performing clinician engagement analytics.

In a particular embodiment, the clinician application includes a Perpetual Tumor Board (PTB), which is a mobile application with its companion cloud based software designed to create an interdisciplinary mobile virtual tumor board. In further embodiments, the resulting ongoing discussion leads to optimal treatment planning, freeing teams and patients from the constraints of current communication tools and the limitation of the face-to-face (F2F) encounters. In various embodiments, components of the PTB include:

A secure online collaboration space where a summary of the patient's clinical information is visible to all HCPs;

A clear list of performed and upcoming testing and interventions visible to all provider team members. This can serve as an interconnector between different EHRs;

A robust collaboration environment where doctors can leave text, voice, and photo messages to the treatment team, a specific physician, HCP, or the patient;

A lightweight project management system running in the background to alert physicians and other HCPs of important milestones or events, such as whether a patient is ready to begin a treatment phase or when a new doctor being added to the team to provide additional consultation;

Integration with EHR systems so clinical information, test results, and prescribed procedures can be displayed to HCPs with minimal manual entry;

An analytic system that checks planned procedures against NCCN standard and alerts doctors if any procedure appears to be outside the standards and will also alert doctors of applicable clinical trials; and/or An app that is HIPAA-compliant insuring patient confidentiality and the safety of their records.

Figure 2:
Figure 5:
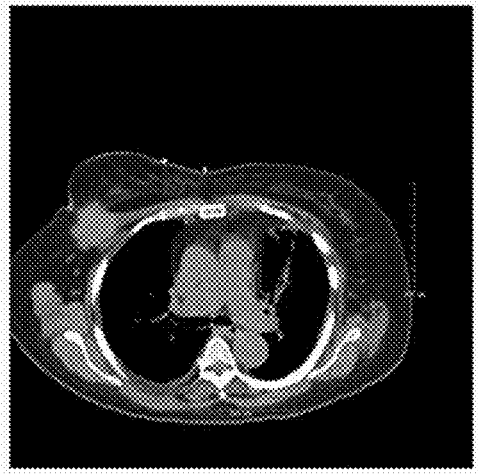
FIG. 5 is a non-limiting example of a graphic user interface, in this case, a mobile clinician application GUI including an interdisciplinary collaboration environment with features for responding to a clinical poll for a particular clinical project.
Figure 8:
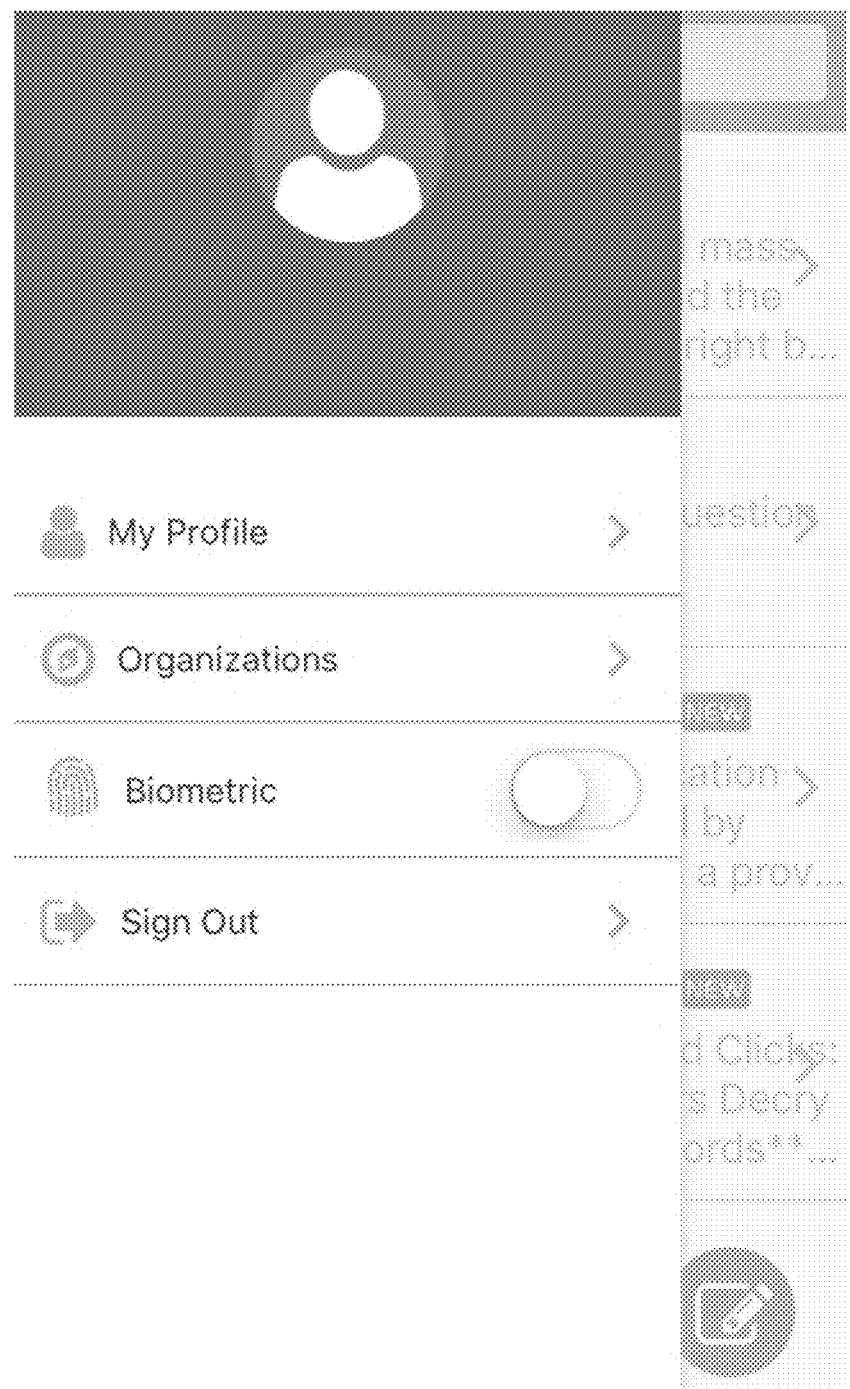
FIG. 8 is a non-limiting example of a graphic user interface, in this case, a mobile clinician application GUI including features for configuring account settings.

FIG. 1 shows an exemplary application icon for a mobile clinician application described herein. In this example, the application icon includes a notification badge indicating to a user that one or more messages have been received and are awaiting review. FIGS. 2-8 show exemplary user interfaces for a mobile clinician application described herein. FIG. 2 shows an exemplary a mobile clinician application interface including features for account creation and log in using a mobile phone number. FIG. 3 shows an exemplary a mobile clinician application interface including features for entering a two-factor account authentication code. FIG. 4 shows an exemplary a mobile clinician application interface including features for accessing a plurality of clinical projects. In this example, the interface includes a search tool and a list of clinical projects, wherein each project includes a representative image, a title, and a preview of a most recent message. FIG. 5 shows an exemplary a mobile clinician application interface including an interdisciplinary collaboration environment. In this example, the interdisciplinary collaboration environment displays a project title, a clinical image, patient background information and an interactive poll presented to clinical users. In this case, the interface further displays the author of the poll, as well as a date and time for the poll, and asks other clinical users to answer a question about a therapeutic option for the patient in light of the clinical details of that patient's condition. FIG. 6 shows an exemplary a mobile clinician application interface including an interdisciplinary collaboration environment. In this example, the interdisciplinary collaboration environment displays a message thread for a clinical project. In this example, each message in the message thread includes an author, a date, and a preview of the message. The messages in this example include text as well as audio (voice) messages. Further, in this example, the messaging interface incudes a text entry field to create a new message in the thread. FIG. 7 shows an exemplary a mobile clinician application interface including an interdisciplinary collaboration environment with features for recording a voice message for a particular clinical project such as a record button and a cancel button. In this example, the title and representative image for the clinical project is displayed along with the recording tools. FIG. 8 shows an exemplary a mobile clinician application interface including an interdisciplinary collaboration environment with features configuring account settings such as user profile, user organizations, and biometric profiles.

Patient Portal

In some embodiments, the platforms, systems, media, and methods described herein include a patient portal. In further embodiments, the patient portal comprises a software module providing a patient help center including a messaging service, a list of performed and upcoming clinical procedures, and/or a notification service for the patient. In some embodiments, the patient portal is implemented as Avident Patient Connect, which is a mobile-enabled web application that complements the PTB to allow patients to communicate with their care providers. In various embodiments, components of the Patient Connect web application include:

An invitation-only mobile webpage that can be opened from an email or SMS text message sent directly from the doctor to the patient;

Verification of credentials to create secure account;

A clear list of performed and upcoming procedures in a form the patient can easily use to track their progress and anticipate future appointments;

Alert and/or reminders of important information from doctors;

A robust help center where patients can get quick response to standard questions, or leave text, voice, and photo messages for the doctor to respond;

An underlying system which alerts doctors of patient communication using SMS text, push notifications, as well as integration with existing office call centers; and/or A Patient Connect web application that is HIPAA-compliant.

Administrative Dashboard

In some embodiments, the platforms, systems, media, and methods described herein include an administrative dashboard. In further embodiments, the administrative dashboard is implemented as a secure website that allows program leaders to collect data on patient profiles, upcoming procedures, rate of guideline compliance, and other key metrics and milestones in the patient's treatment. This will allow leaders to monitor quality, cost and to more efficiently manage resources.

Figure 9:
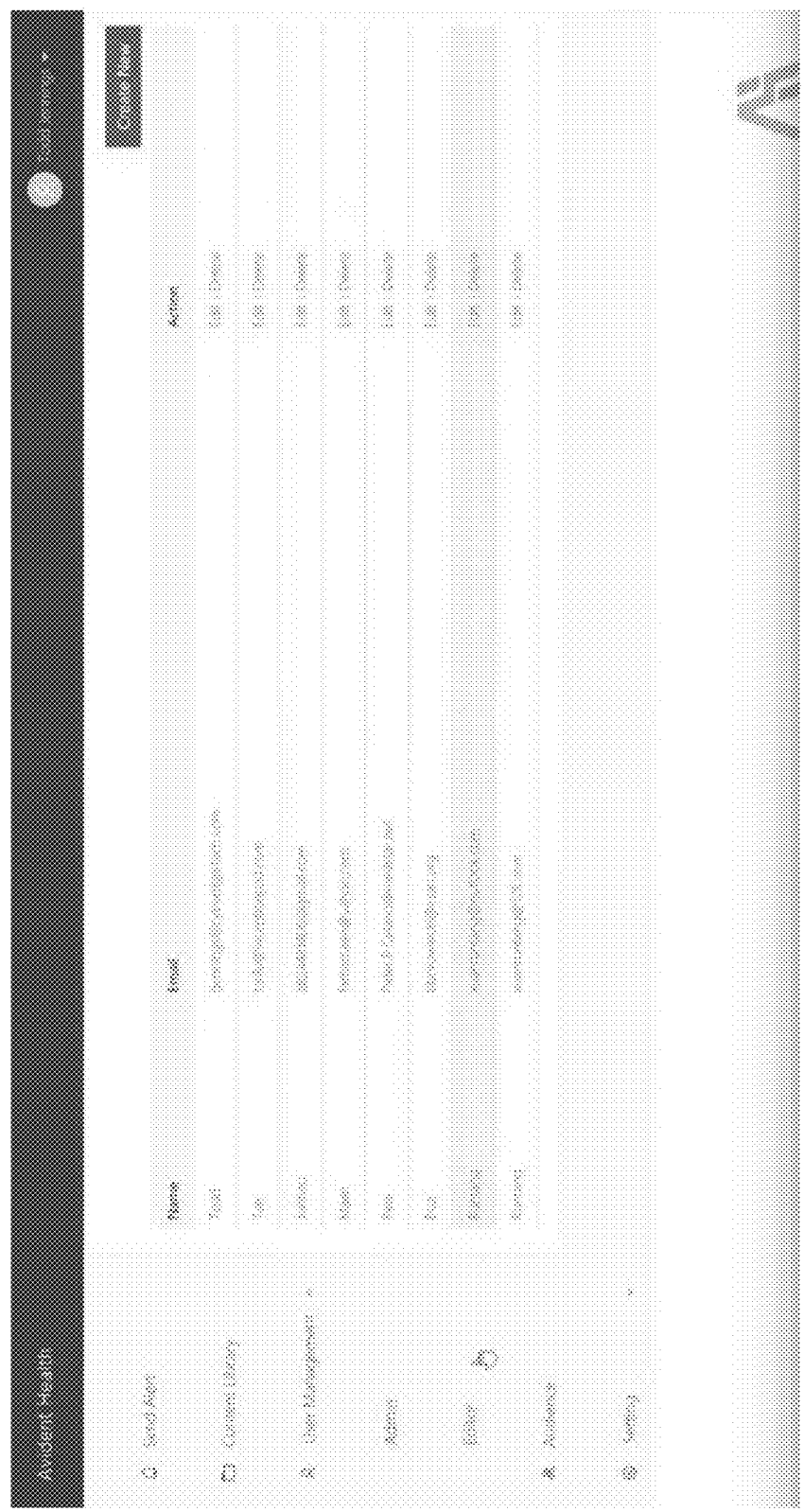
FIG. 9 is a non-limiting example of a graphic user interface, in this case, an administrative dashboard application GUI including features for user management.
Figure 10:
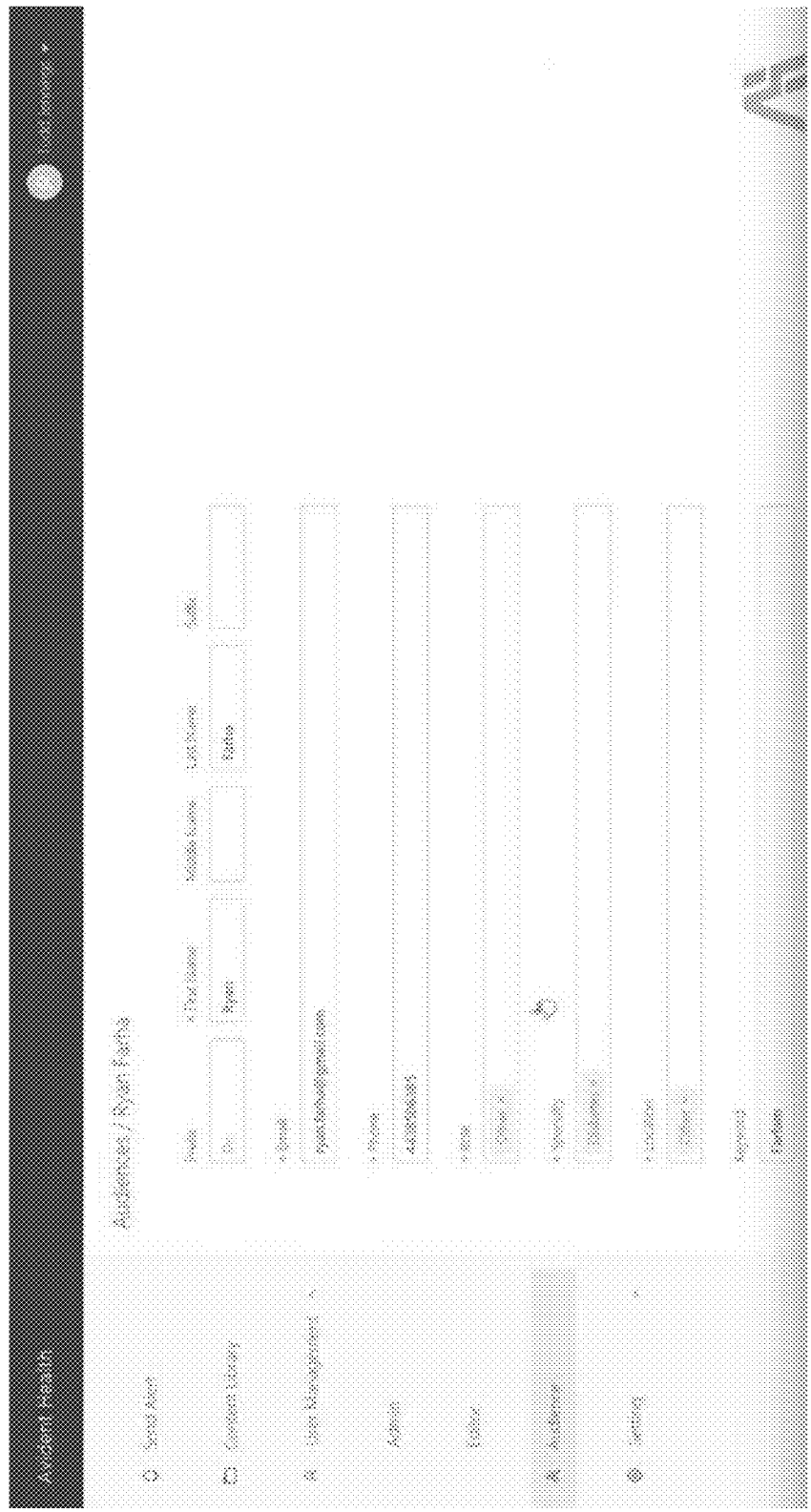
FIG. 10 is a non-limiting example of a graphic user interface, in this case, an administrative dashboard application GUI including features for editing a user profile.
Figure 11:
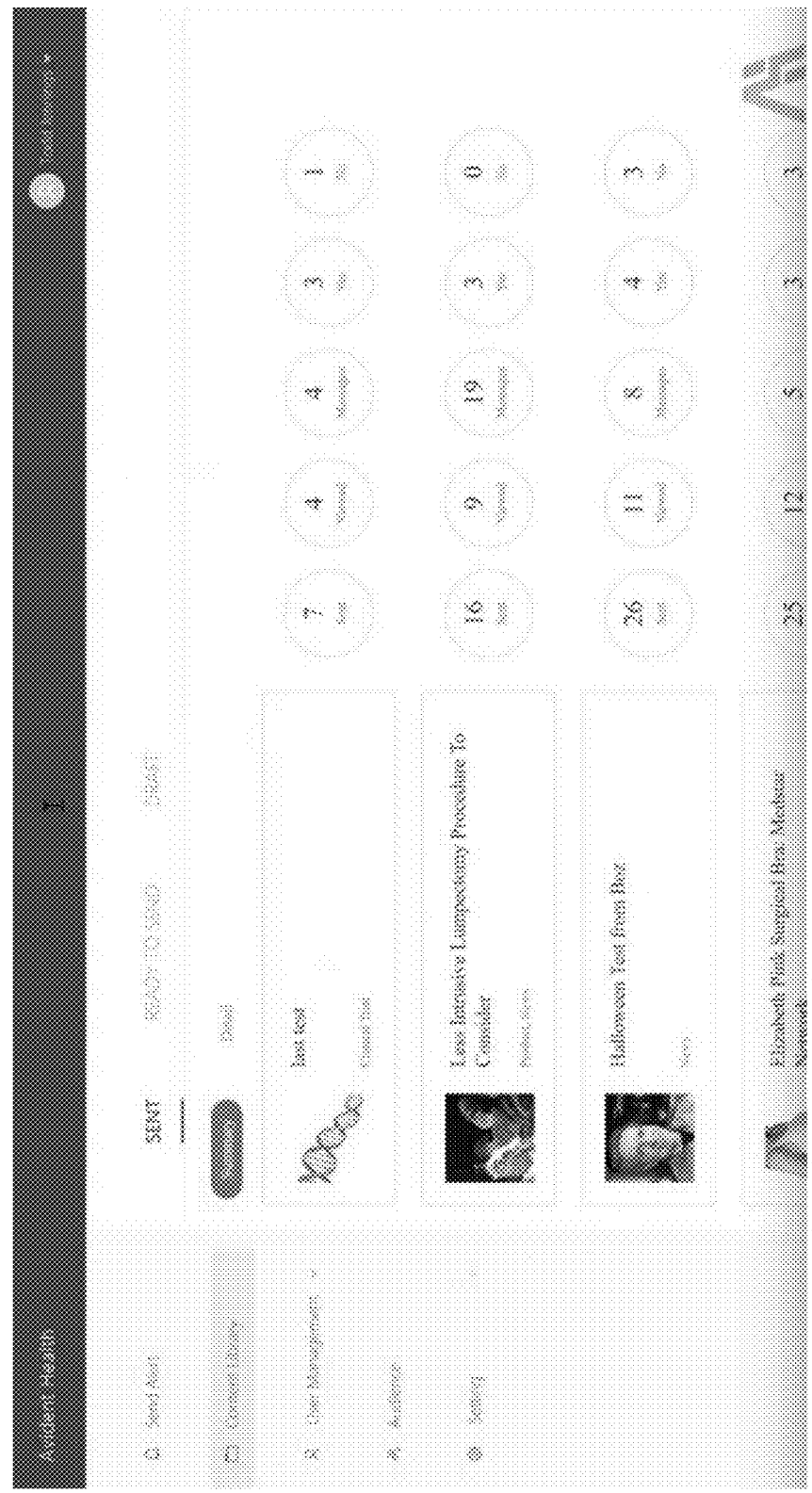
FIG. 11 is a non-limiting example of a graphic user interface, in this case, an administrative dashboard application GUI including features providing a content dashboard showing levels of user engagement with each content item.
Figure 12:
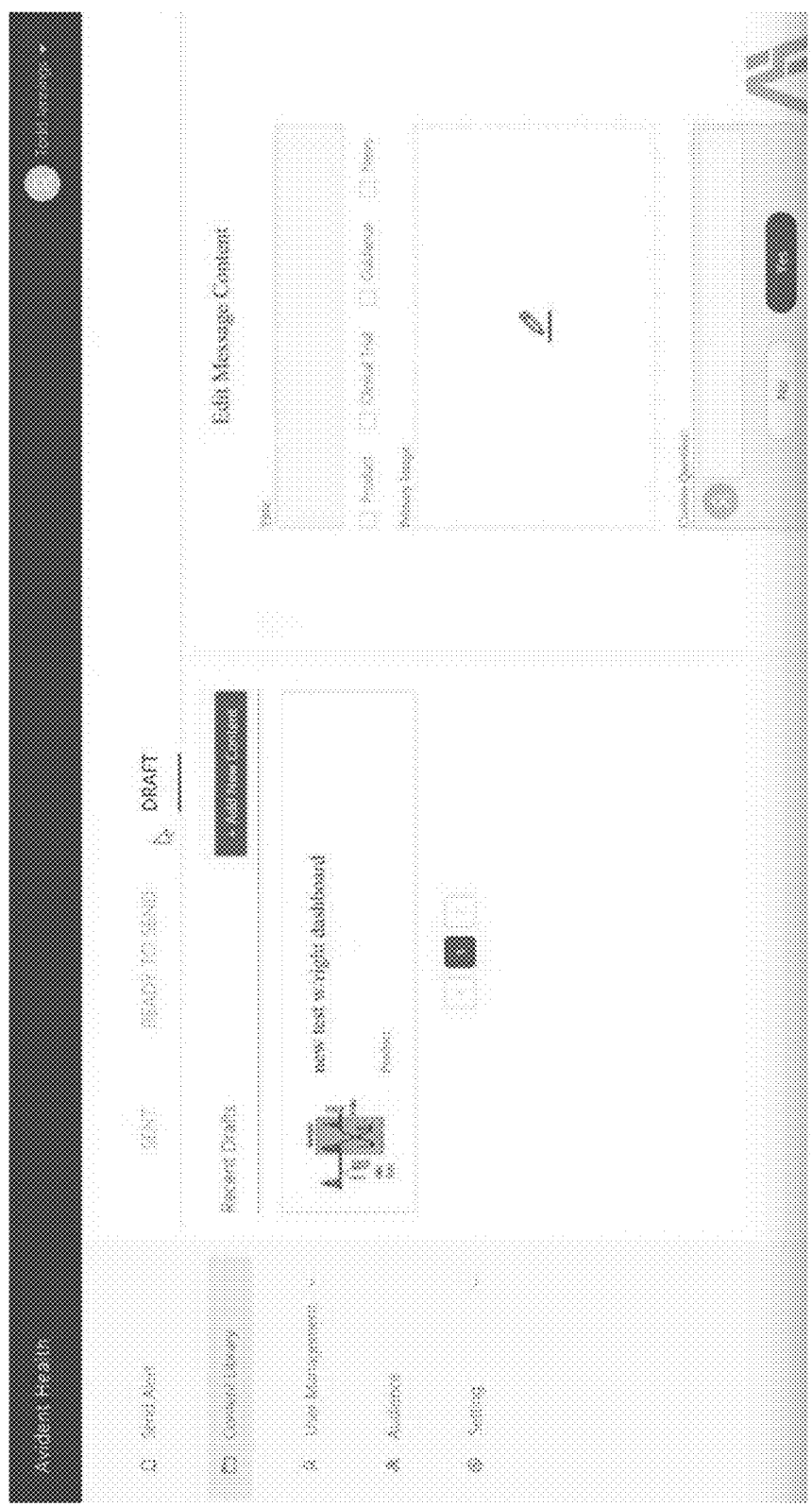
FIG. 12 is a non-limiting example of a graphic user interface, in this case, an administrative dashboard application GUI including features for viewing and editing draft messages.
Figure 13:
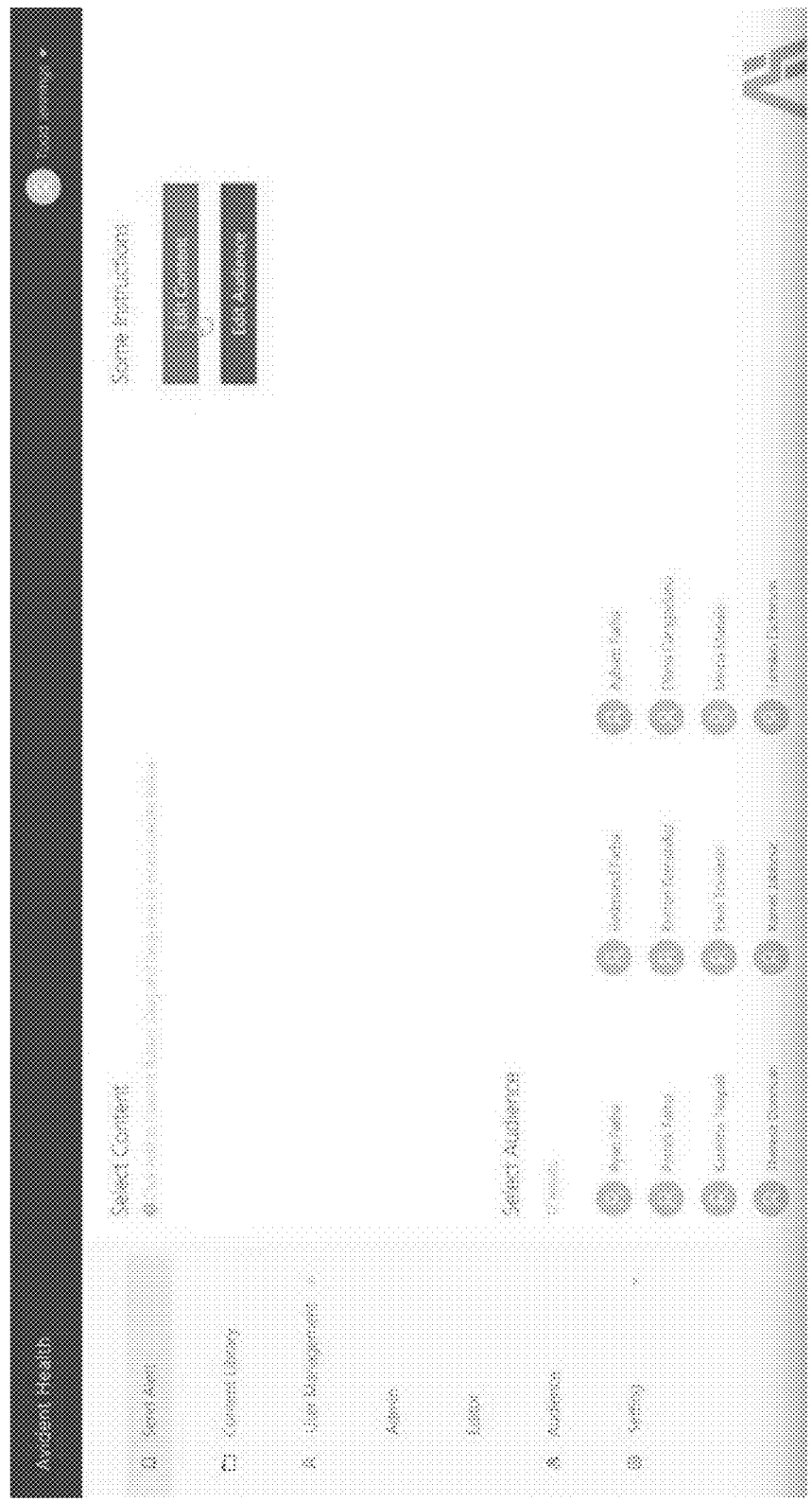
FIG. 13 is a non-limiting example of a graphic user interface, in this case, an administrative dashboard application GUI including features for creating a new message.
Figure 14:
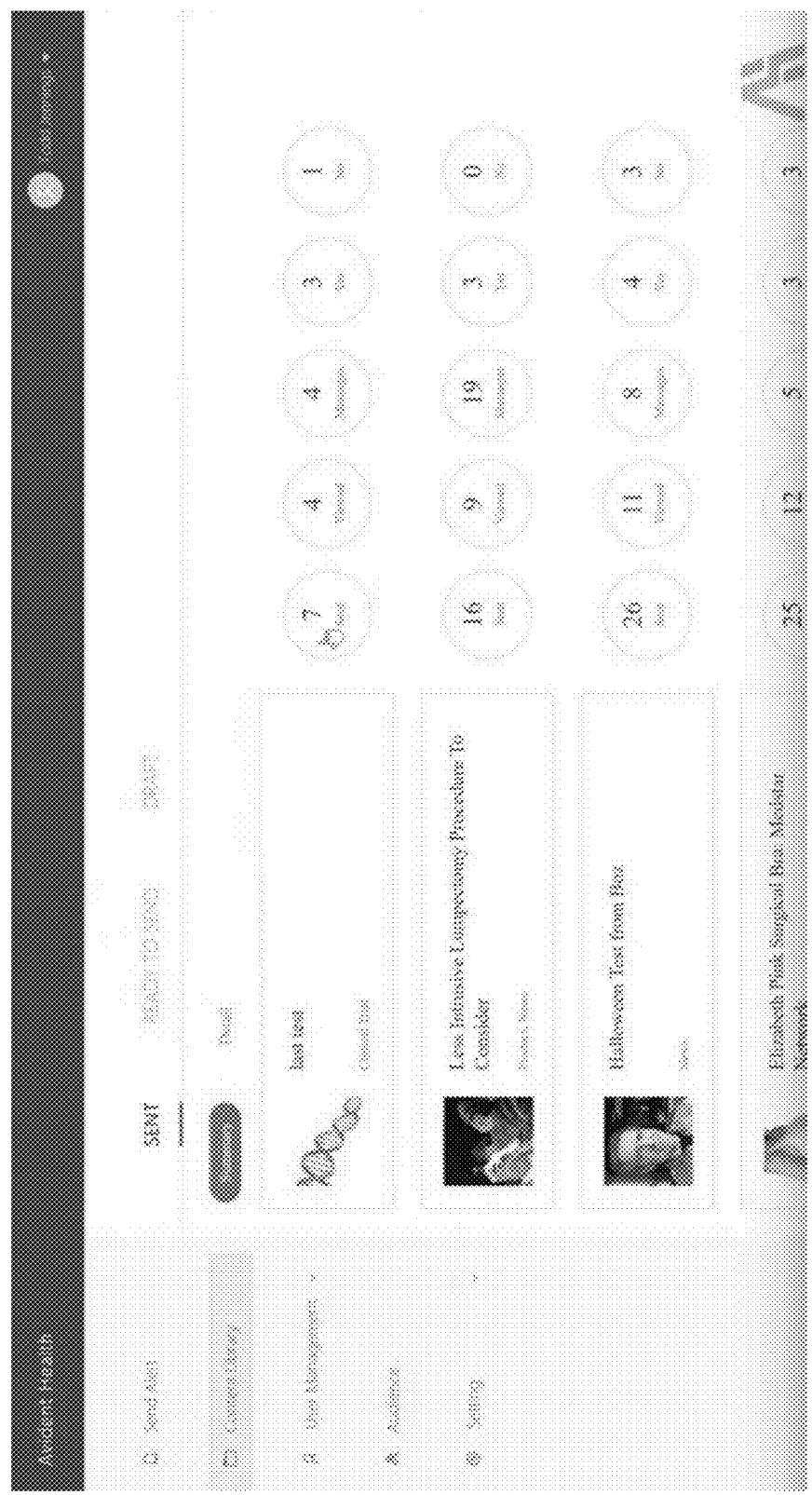
FIG. 14 is a non-limiting example of a graphic user interface, in this case, an administrative dashboard application GUI including features for viewing sent messages.
Figure 15:
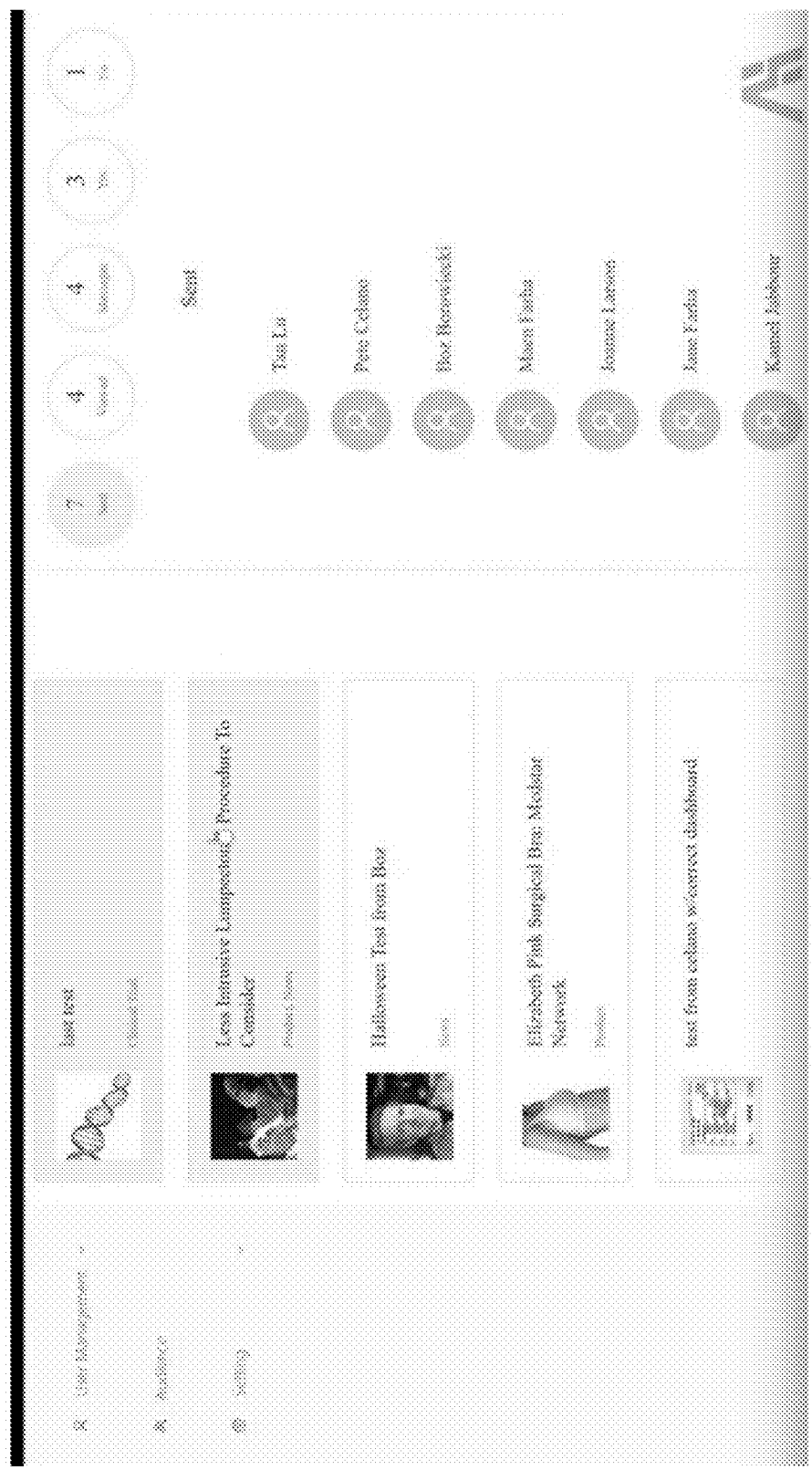
FIG. 15 is a non-limiting example of a graphic user interface, in this case, an administrative dashboard application GUI including features for presenting recipient properties of a particular sent message.
Figure 16:
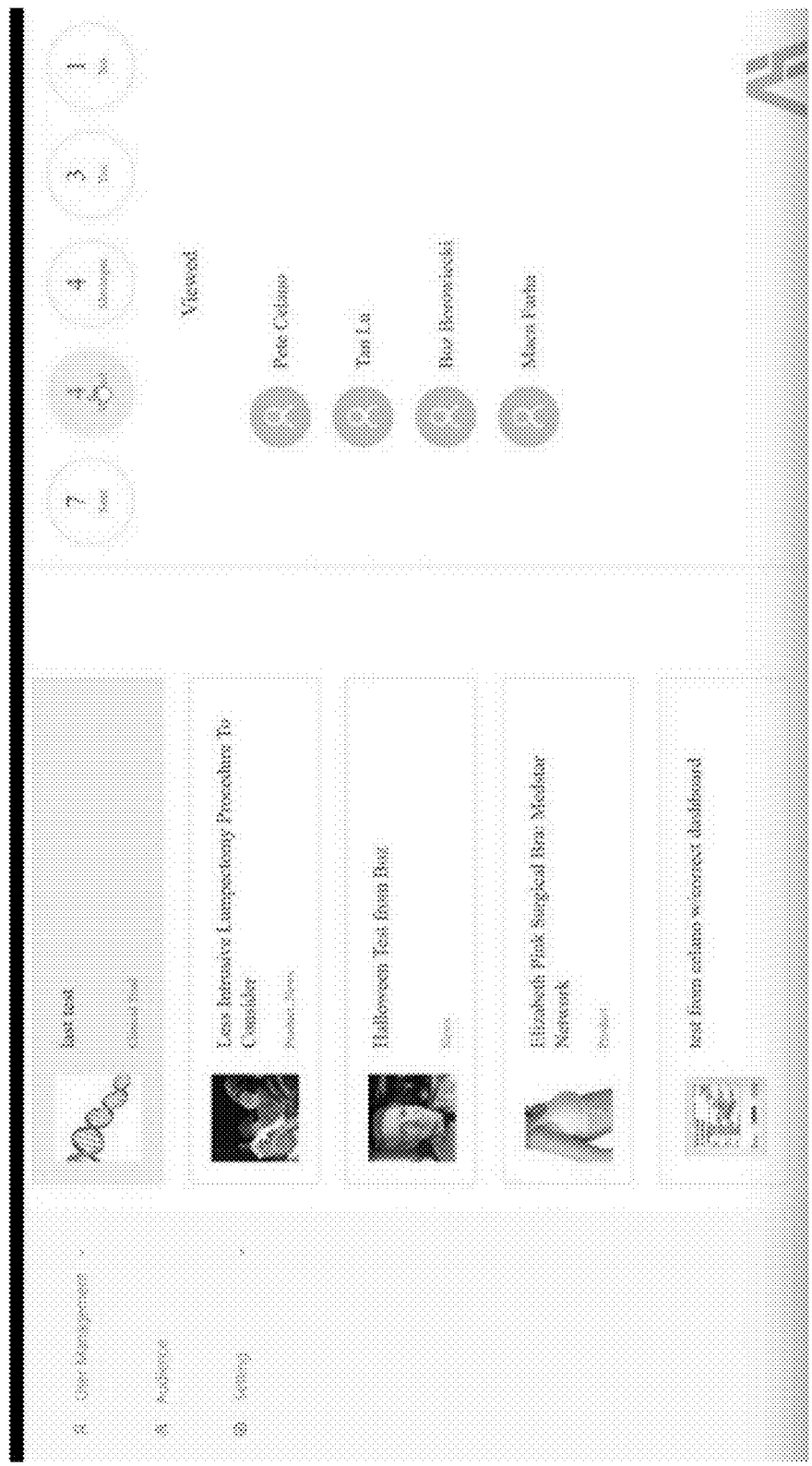
FIG. 16 is a non-limiting example of a graphic user interface, in this case, an administrative dashboard application GUI including features for presenting viewing properties of a particular sent message.
Figure 17:
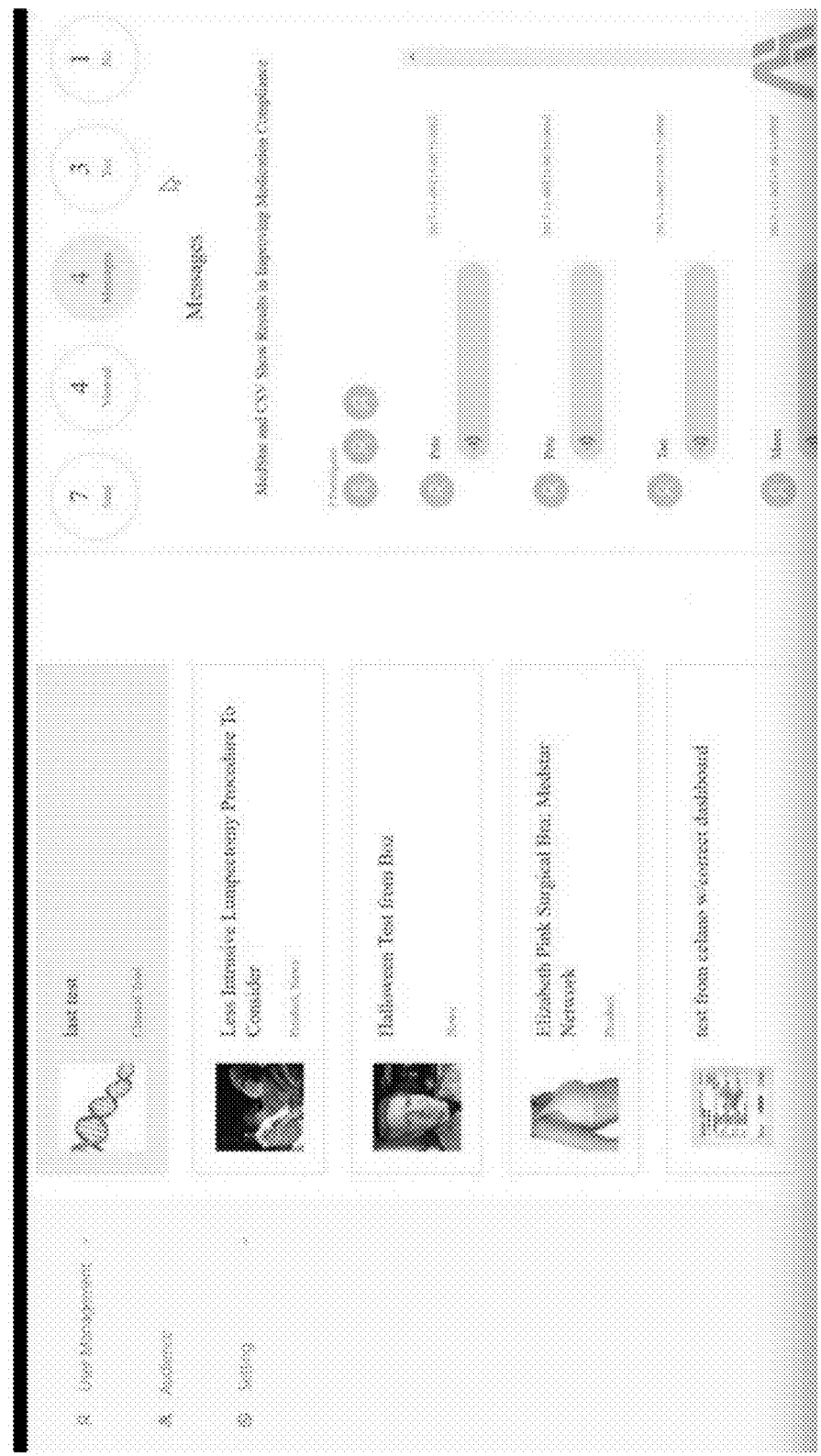
FIG. 17 is a non-limiting example of a graphic user interface, in this case, an administrative dashboard application GUI including features for presenting messaging properties of a particular sent message.
Figure 18:
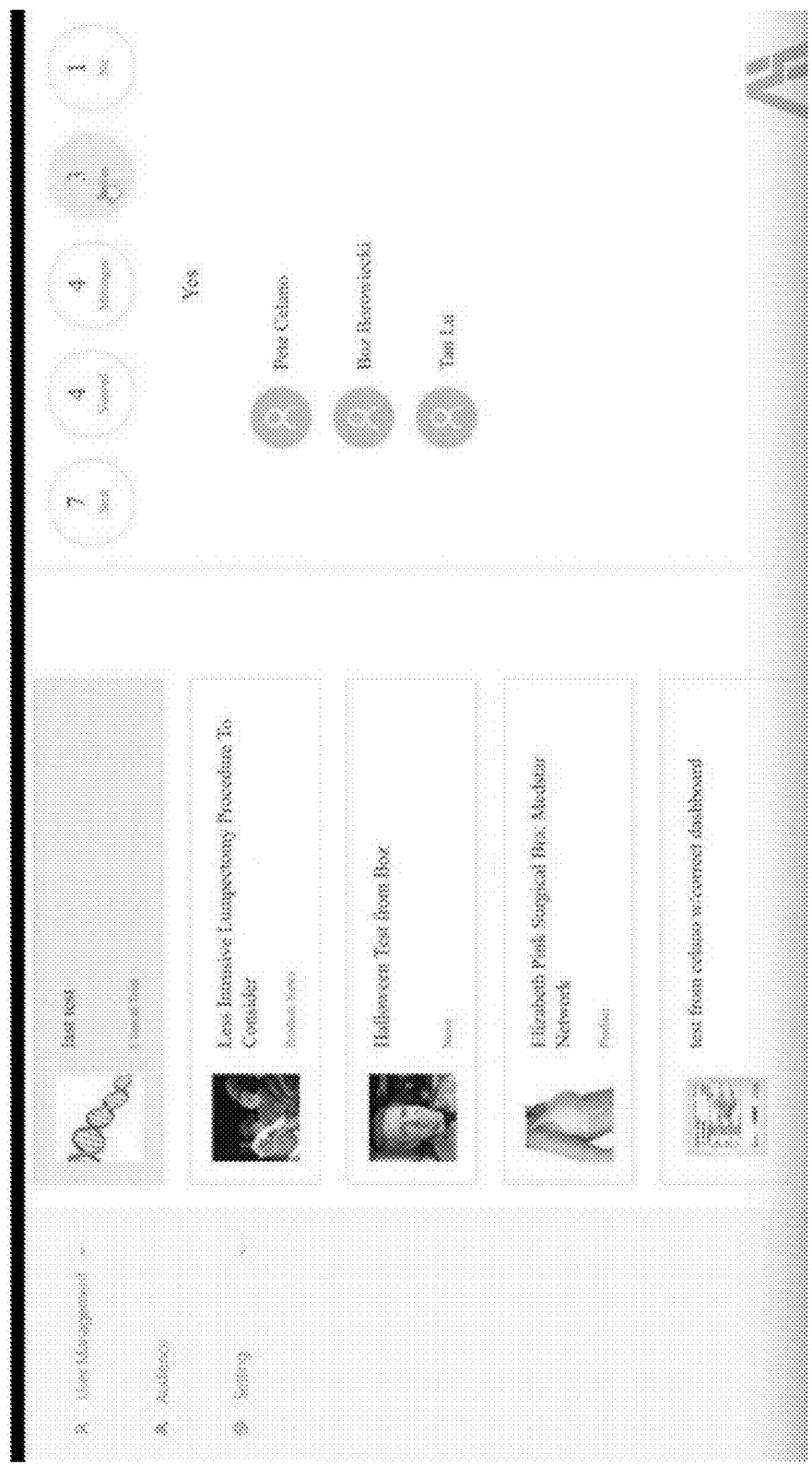
FIG. 18 is a non-limiting example of a graphic user interface, in this case, an administrative dashboard application GUI including features for presenting polling properties of a particular sent message.

FIGS. 9-19 show exemplary user interfaces for an administrative dashboard application described herein. FIG. 9 shows an exemplary administrative dashboard application interface. In this example, the interface includes tools for user management. In this example, the tools for user management allow an administrative user to add users and edit user profiles. FIG. 10 shows an exemplary administrative dashboard application interface including tools for editing the details of a user profile such as name, phone number, email, role in the clinical project, clinical specialty, location, and the like. FIG. 11 shows an exemplary administrative dashboard application interface including a content library. In this example, the content library displays levels of user engagement with each content item in terms of number of users to whom the item was sent, the number of user who have viewed the content item, the number of messages posted about the content item, and the numbers of answers to polls in both the affirmative and the negative. FIG. 12 shows an exemplary administrative dashboard application interface including tools for viewing and editing draft messages as well as creating new messages. In this example, the interface includes features for adding or editing the content for a message. FIG. 13 shows an exemplary administrative dashboard application interface including tools for creating a new message. In this example, the interface includes features for editing and selecting both content for the new message and the audience for the new message. FIG. 14 shows an exemplary administrative dashboard application interface including a list of sent content items. In this example, the interface includes indicators of the level of user engagement with each sent content item in terms of number of users to whom the item was sent, the number of user who have viewed the content item, the number of messages posted about the content item, and the numbers of answers to polls in both the affirmative and the negative. FIG. 15 shows an exemplary administrative dashboard application interface including tools for viewing recipient properties of a particular sent message. In this example, the recipient properties include a list of users to whom the content item was sent. FIG. 16 shows an exemplary administrative dashboard application interface including tools for viewing the view properties of a particular sent message. In this example, the view properties include a list of users who have viewed the content item. FIG. 17 shows an exemplary administrative dashboard application interface including tools for viewing messaging properties of a particular sent message. In this example, the messaging properties include a list of the messages sent pertaining to the content item. FIG. 18 shows an exemplary administrative dashboard application interface including tools for viewing polling properties of a particular sent message. In this example, the polling properties include a list of users answering a poll in the affirmative. In other embodiments, the polling properties include a list of users answering a poll in the negative.

Figure 19:
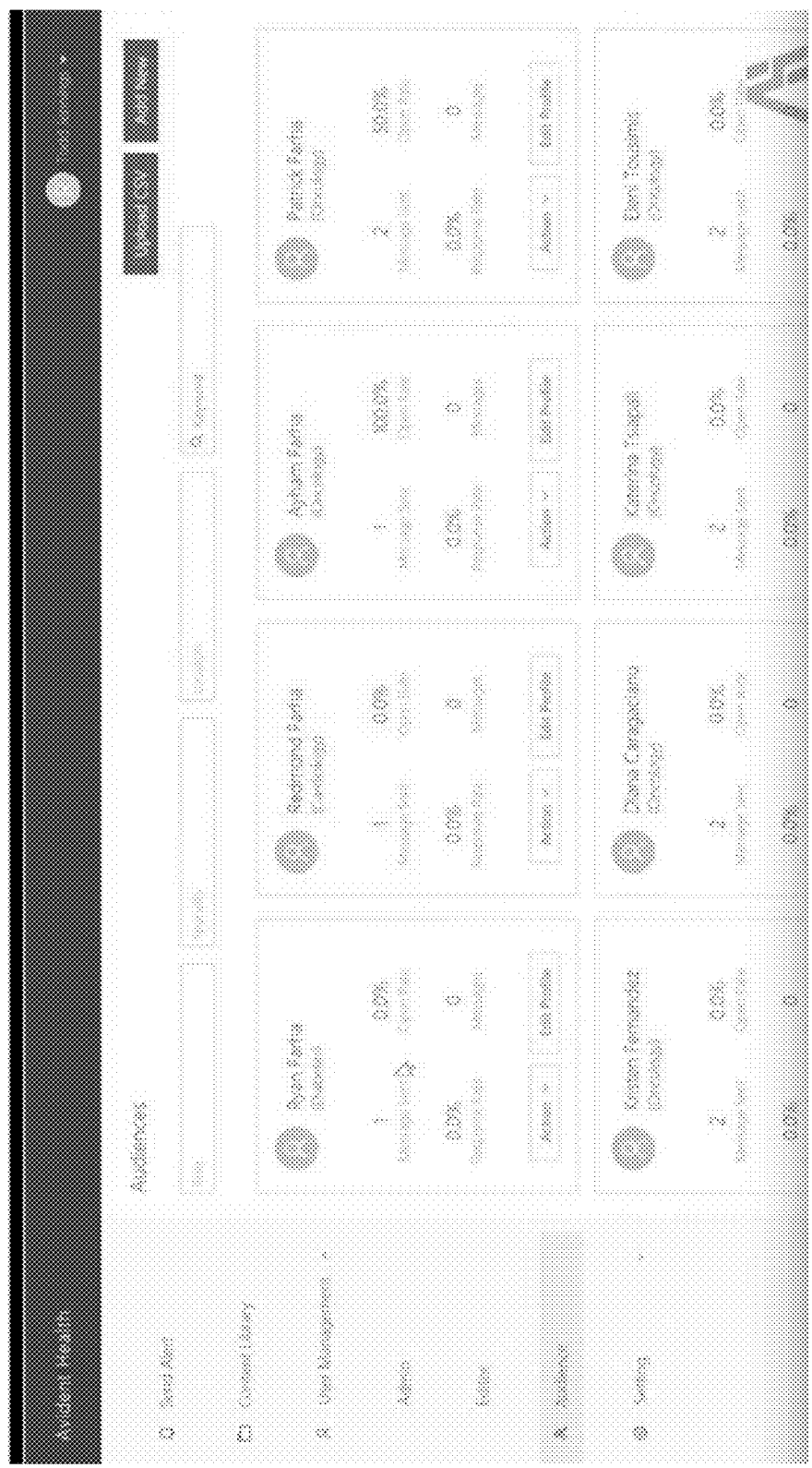
FIG. 19 is a non-limiting example of a graphic user interface, in this case, an administrative dashboard application GUI providing a user analytics report.

FIG. 19 shows an exemplary administrative dashboard application interface. In this example, the interface includes a detailed user analytics report. Further, in this example, the user analytics report includes tools to search user analytics data by, for example, role, specialty, location, and keyword. The user analytics report of FIG. 19 includes, for each user, number of messages sent, message open rate, messages response rate, and the like.

Notation Module

In some embodiments, the platforms, systems, media, and methods described herein include an aggregated relevant decision driving engine including a notation module. In further embodiments, the notation module is configured to express relationships between patient treatment steps. In still further embodiments, the notation module is configured to express relationships between patient treatment steps in a human-readable and human-editable form. In a particular embodiment, the notation module expresses relationships between patient treatment steps a one or more node-and-arc diagrams. In some embodiments, the notation module is configured to transmit an output as readable instructions to a native inference engine described herein, a supervised machine learning algorithm described herein, or both.

In some embodiments, the notation module follows the rules of a symmetric or non-symmetric, sequential or non-sequential, influence or relevance diagram with decision nodes and event nodes that are derived from a treatment guideline and subsequently edited through human input and through machine inference techniques.

Figure 20:
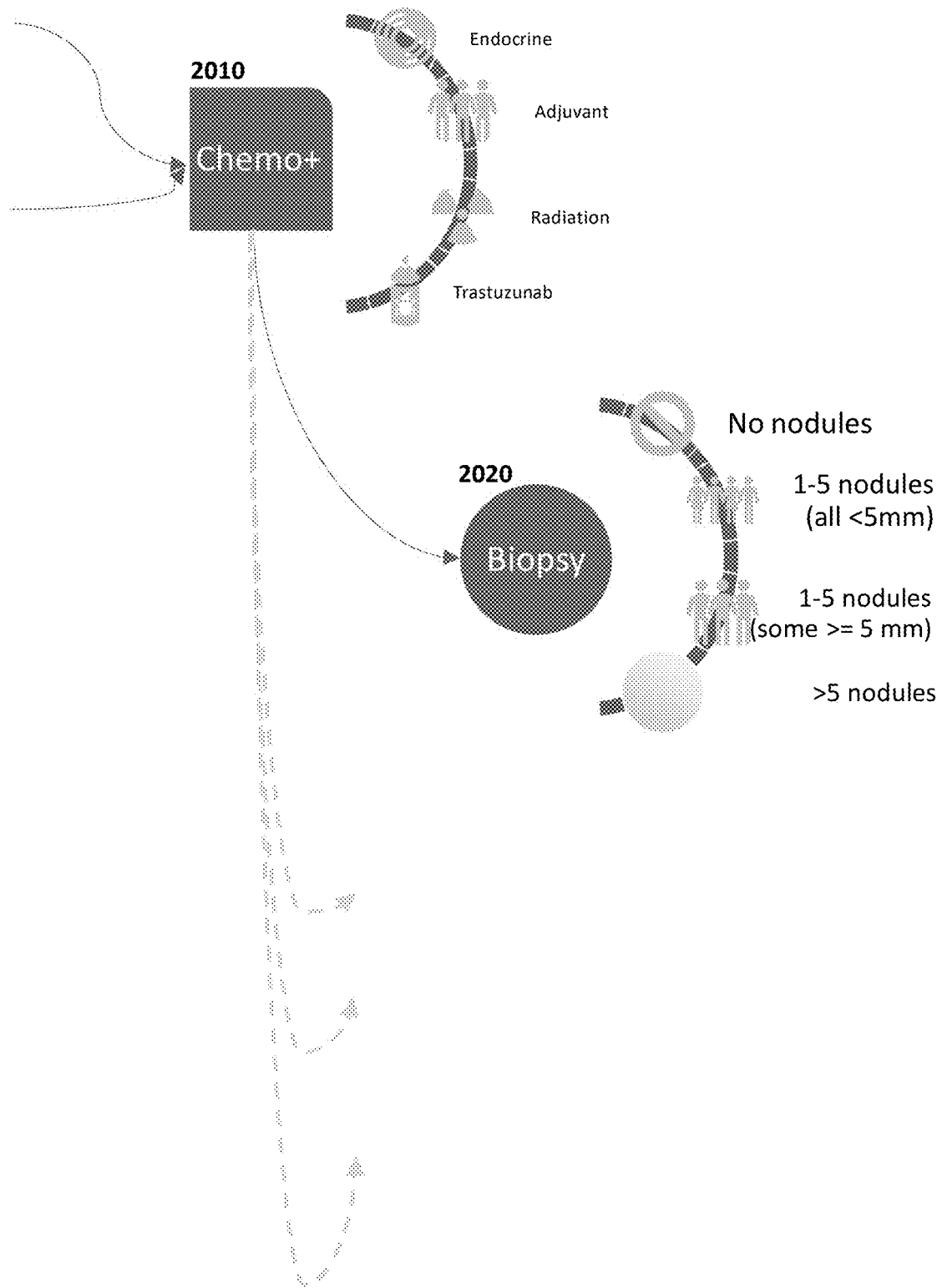
FIG. 20 is a non-limiting example of notation for decision nodes and event nodes, which constitute components of an exemplary relevance/inference network described herein.

Referring to FIG. 20, in a particular embodiment, the node-and-arc network that is variously used for notation, translation inference, learning would consist of nodes that denote decision 2010, nodes that denote events 2020, and arcs connecting them that denote relevance, influence, sequential occurrence or any other relationship.

In some embodiments, the notation module is derived from the invention described in U.S. Pub. No.2016/0012189.

Translation Module

In some embodiments, the platforms, systems, media, and methods described herein include an aggregated relevant decision driving engine including a translation module. In further embodiments, the translation module is configured to express aggregated electronic medical records in a format that is human-readable. In still further embodiments, the translation module is configured to make aggregated electronic medical records accessible to a native inference engine described herein, a supervised machine learning algorithm described herein, or both.

In further embodiments, the past progress of a patient is mapped to a distinct node on the relevance diagram by the supervising physician, with or without machine assistance, and with automated or manual amendments to the network if the particular patient's progress deviates from the pathways previously encompassed in the guideline are previously represented in the notation module.

Real-Time Tumor Registry With Distributed Ledger

In some embodiments, a public/private key encryption scheme and method with a permissioned blockchain is used to identify and group decisions, events demographic information, and medical histories pertaining to the same patient without allowing the identity of the patient to be revealed to any user who is not also a physician treating that patient and entitled to view her identity.

Figure 21:
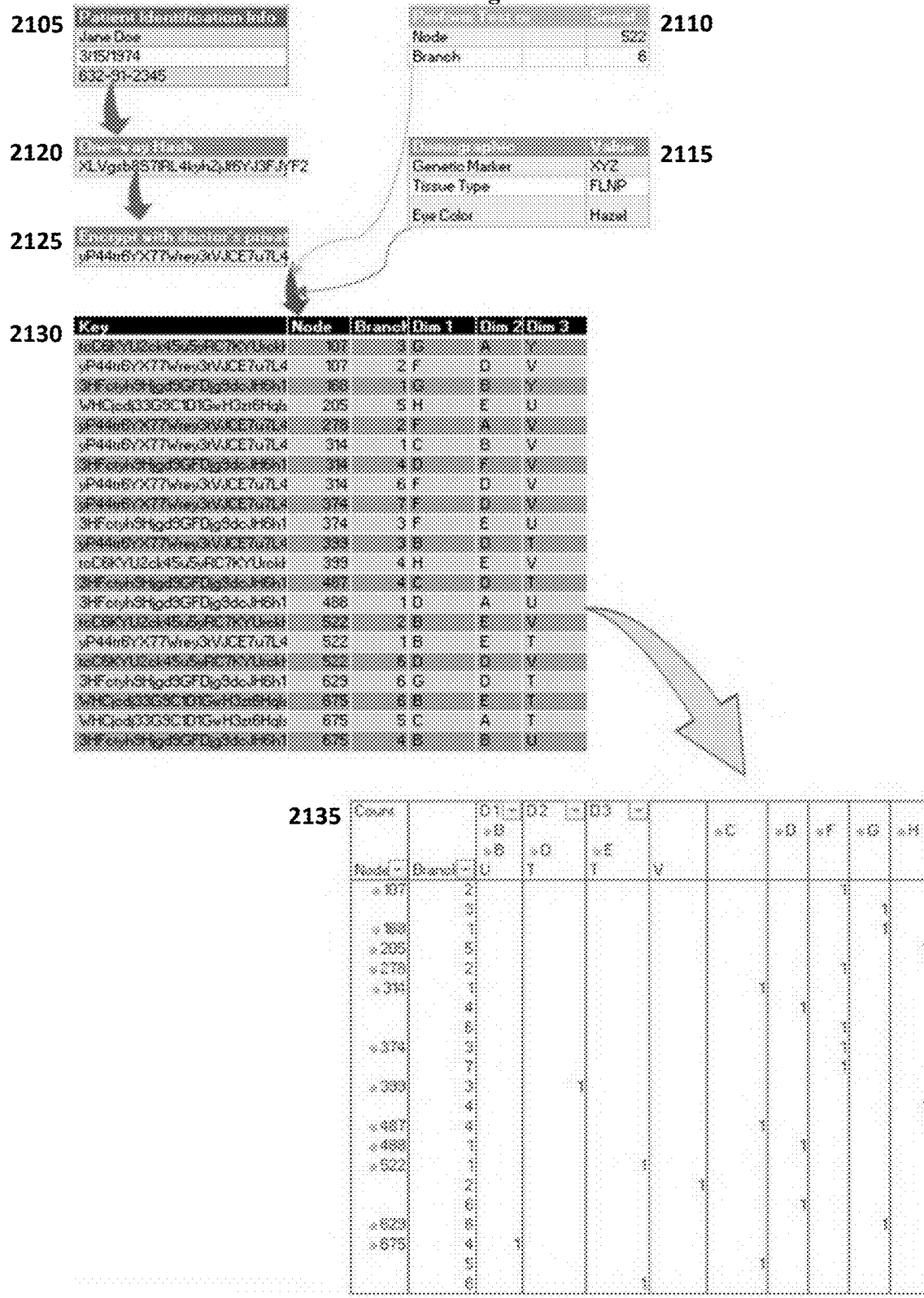
FIG. 21 is a data conversion diagram illustrating how confidential information is encrypted for cross referencing purposes then discarded for input into the relevance/inference network.
Figure 22:
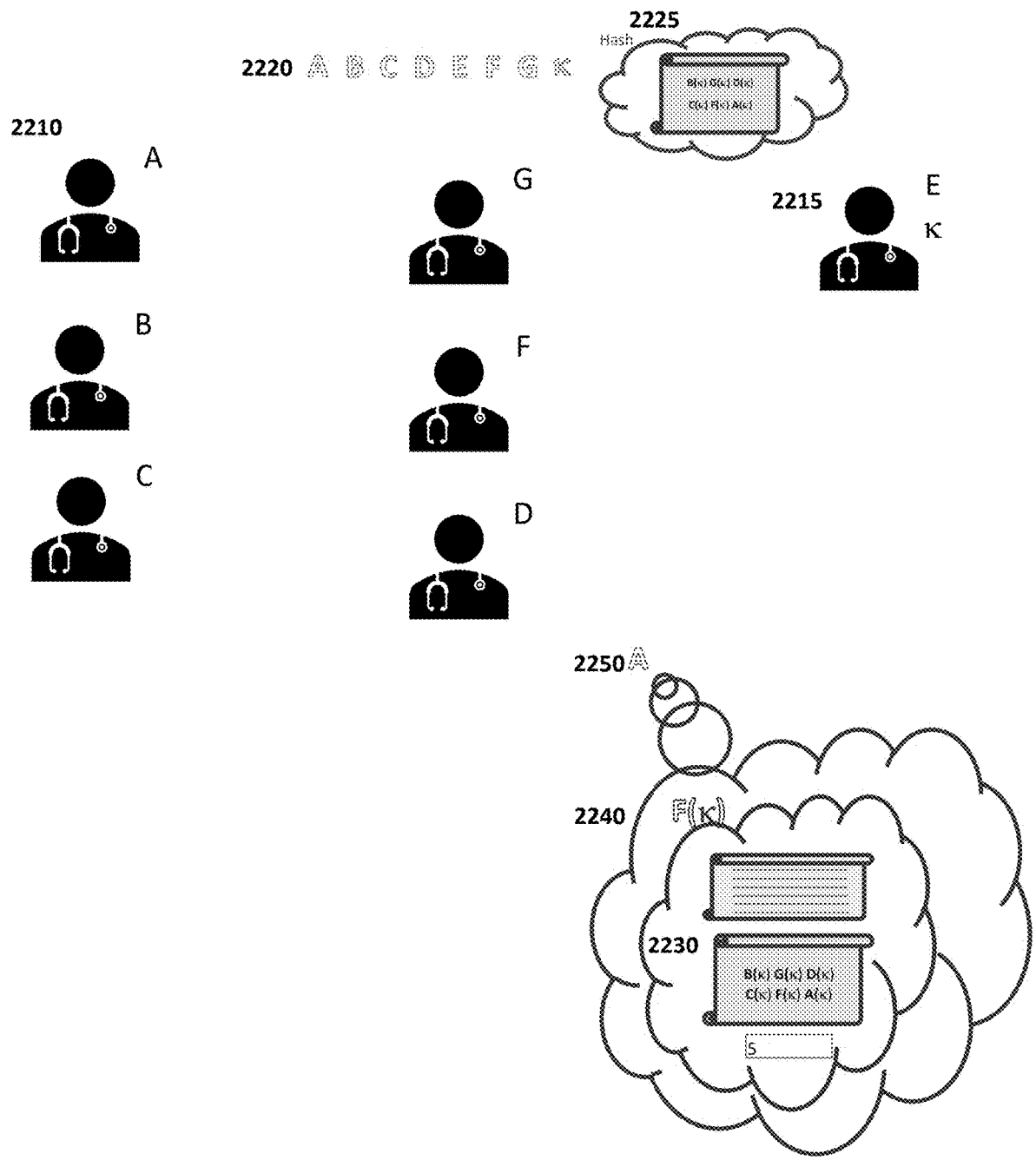
FIG. 22 is a block diagram illustrating a sample network of seven physicians, including one custodian, with public/private encryption keys and showing the flow and encryption pattern of information in the first step of the deanonymization scheme.
Figure 23:
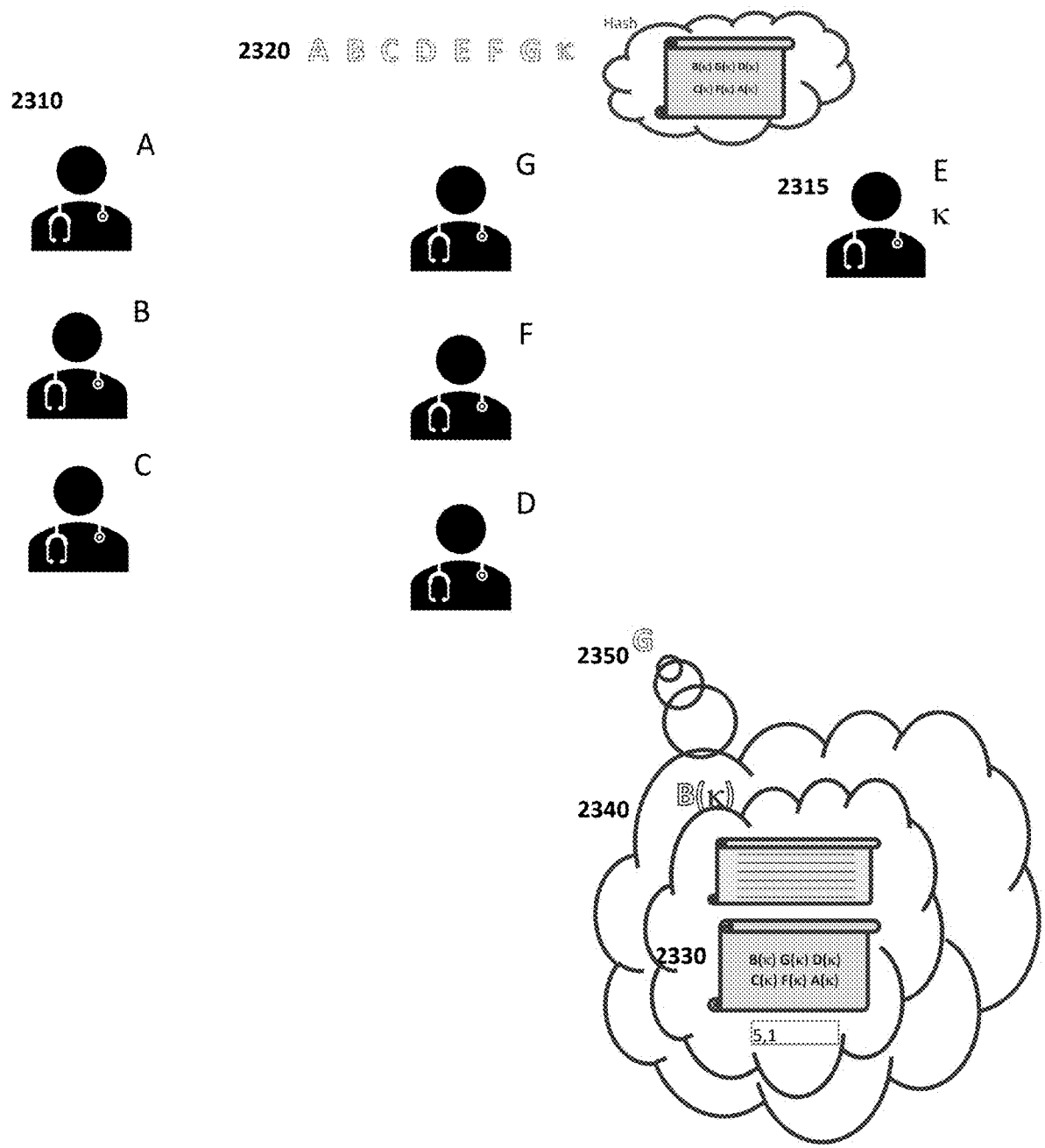
FIG. 23 is a block diagram showing the second step of the deanonymization scheme in the same sample network of seven physicians illustrated in FIG. 22.
Figure 24:
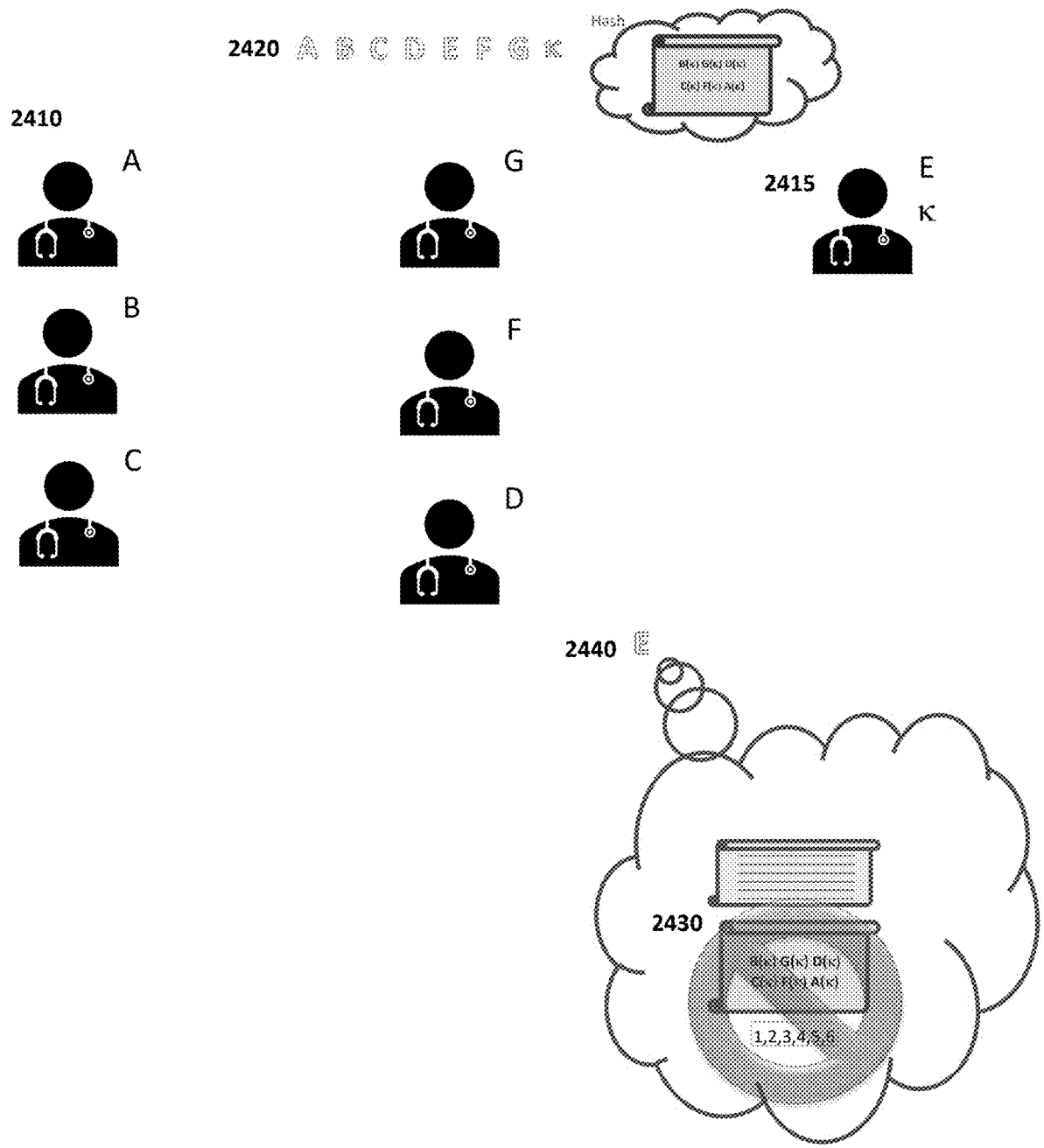
FIG. 24 is a block diagram showing the seventh and last step of the deanonymization scheme in the same sample network of seven physicians illustrated in FIGS. 22 and 24.

Referring to FIG. 21, in some embodiments, the name and personal identifying information of the patient 2105 is stored in an electronic health record viewable by the treating physician and attached to demographic information of potential research interest 2115 and medical information comprising tests, treatments and results among other things 2110. Before transmitting any information to the real-time tumor registry, the identifying information is encrypted first with a one-way hash 2120 and then with the public key of the physician 2125. This allows a different physician who also has different information on the same patient, but not any other physician in the system, to determine the identity of the physician loading the latest information, so the records can be reconciled in a master table 2130. Periodically, a block of new information added to the master table 2130 and reconciled with the above-described process is summarized into a pivot table 2135 and may be re-encrypted with a time-sensitive key by a randomly assigned system user with permission to re-encrypt blocks.

Inference Network

In some embodiments, the platforms, systems, media, and methods described herein include an aggregated relevant decision driving engine including a native inference network. In further embodiments, the native inference network is configured to receive inputs from one or more medical records of a patient. In still further embodiments, the native inference network is configured to receive a subset of interlinked treatment steps selected by the treating physician. In some embodiments, the native inference network is configured to generate outputs comprising predictions and probabilities pertaining to the treatment of the patient.

In some embodiments, the real-time tumor registry is used to update the probabilities derived from pre-existing public tumor registries and using a Bayesian calculation that takes into consideration the sizes of the populations used to calculate both the prior and the posterior probability. In cases where the updated probabilities pertain only to a subset of patients, new nodes or new arcs may be added to the relevance diagram to reflect this using the same notation from the notation module

Machine Learning Algorithm

In some embodiments, the platforms, systems, media, and methods described herein include an aggregated relevant decision driving engine including a machine learning algorithm. In further embodiments, the machine learning algorithm is a supervised machine learning algorithm. In some embodiments, the supervised machine learning algorithm is configured to read medical records of a plurality of patients. In further embodiments, the supervised machine learning algorithm is configured to aggregate medical records of a plurality of patients. In still further embodiments, the supervised machine learning algorithm is configured to combine aggregated medical records with one or more tumor registries to test hypotheses about the efficacy of potential courses of treatment for particular subsets of patients.

In some embodiments, the machine learning algorithm is based on Bayesian Inference Networks. With the information encoded in the real-time registry and the relevance network, heuristics such as greedy search, constrained search, branch and bound, genetic algorithms and neural networks are used to attempt to derive different configurations of the nodes and their arcs that may increase the predictive power of the relevance network or reduce the network's complexity while maintaining the same predictive power. In some embodiments, a consensus or majority or hierarchical process can be used to introduce human evaluation and scoring of alternatives to train the machine learning algorithm and to promulgate new findings from the machine learning algorithm to all system users.

Exemplary Architectures

The platforms, systems, media, and methods described herein are designed to take advantage of the best technology services available. The different layers and technology work together in a REST API application to provide holistic services that users are able to use in a seamless manner. To meet HIPPA requirements, the architecture can use much of Amazon's HIPPA-certified infrastructure.

Figure 25:
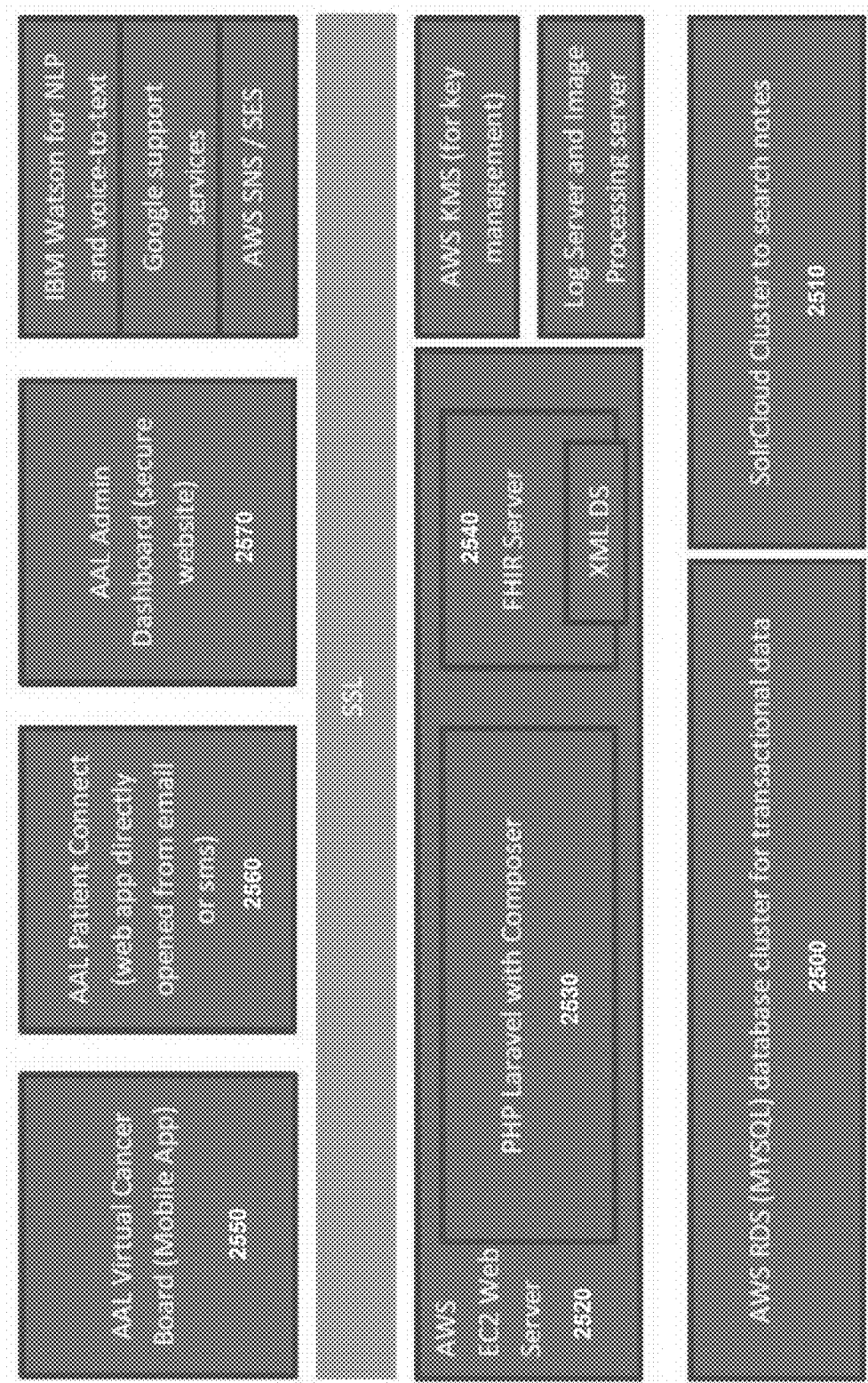
FIG. 25 is a block diagram illustrating a first non-limiting example of a software architecture.

A first exemplary embodiment is illustrated at FIG. 25.

Database Layer: In this embodiment, the system uses three databases: 1) SQL server 2500 for transactional data. All PHI in this example is encrypted in this database; 2) Solr search engine 2510 for text and voice note search. The system in this embodiment does not store PHI in this search engine; and 3) An XML data store for the storage processing and retrieval of XML documents and data sources. SQL server may initially be AWS MySQL but is optionally switched to AWS Oracle. Solr search engine is an implementation of SolrCloud on AWS EC2, and is used for searching non-PHI data only. Further, in this embodiment, the XML data store is only used for transient storage and processing of the EHR records retrieved on demand form the service providers for the patient. All databases in this embodiment are behind an internal load balancer and can only be accessed via internal IP address from authorized servers. The SQL server is the system of record and are backed up daily to disk, and weekly to tape using AWS glacier.

Webserver: The back-end server in this embodiment is AWS EC2 2520 running PHP with the Laravel framework 2530. The servers are optionally implemented in a multi-node cluster running behind AWS's high-availability load balancer. All communication with the webserver requires SSL encryption over HTTPS.

FHIR Server: FHIR Server 2540 in this embodiment is the main engine for integrating with various EHR systems in use by the patient's health care providers. This is optionally a distributed cluster behind an internal load balancer and is designed to retrieve only the records of interest when needed. Each FHIR server in this embodiment includes an embedded XML database to facilitate the manipulation of XML data. No data is stored in this embodiment after it is transformed.

Support Servers and Services: The system of this embodiment has support servers that are only accessible behind the VPN to aggregate logs and perform certain support actions such as cropping images, etc. We optionally use AWS Key Management Service to manage encryption keys.

Mobile Application: The Virtual Cancer Board application 2550 in this embodiment is built using React Native technology. Apple Watch and Android Wear applications are optionally implemented. For wearable devices, in this embodiment, we write the application in native iOS and Android code. The mobile applications run on any iPhone running iOS 8 or above and any Android device running Android operating system 5.0 and above.

Web Application: The web application 2560 in this embodiment is built using the React front-end framework. Use of this technology improves the componentization of the front end and thereby increases the flexibility of the display of records and other content.

Admin Website: The admin website 2570 in this embodiment is a dashboard that is built using React framework as well.

Front-end Support Services: We optionally use IBM Watson for natural language processing to make voice and text notes searchable and to allow the system to provide intelligent response when appropriate. The voice-to-text engine is optionally Watson as well.

Messaging: In this embodiment, we use Amazon SNS service send alert SMS texts, emails, and push notifications.

Figure 26:
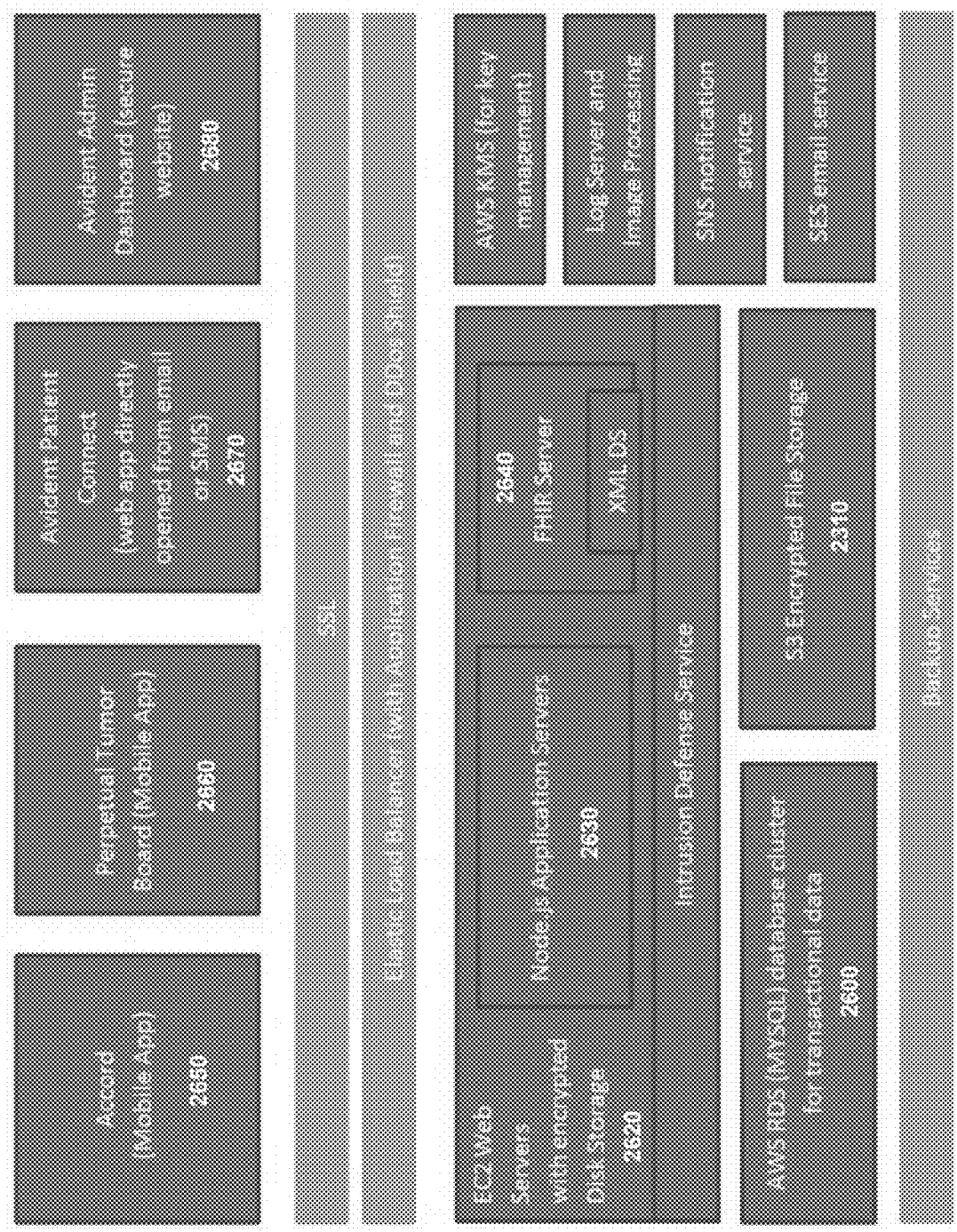
FIG. 26 is a block diagram illustrating a second non-limiting example of a software architecture.

Next, a second exemplary embodiment is illustrated at FIG. 26.

Database Layer: In this embodiment, system uses the AWS RDS database cluster 2600, which is covered by the AWS BAA. This database in this embodiment is encrypted.

All data access to this database is via HTTPS, and the database itself can only be accessed from within the virtual private network by specific servers. This is only one of two places in the described platform that PHI data may be stored at rest. RDS data, in this embodiment, is backed up daily. The database general log, which contains all database connections and complete query history, is sent and stored in AWS CloudWatch in this embodiment.

File Storage Layer: The secured file storage in this embodiment is implemented using AWS S3 2610. All user uploaded documents, voice messages, and photo messages in this embodiment are stored and encrypted in S3. Each access of the requested file goes through an authentication process in this embodiment to retrieve a verification token to decrypt and use the requested file. Because the requirement for retrieving the decryption token, access to S3 files are logged at the application level and correlated to the ID of an authorized application user in this embodiment.

Webserver: The back-end server in this embodiment is AWS EC2 2620 running Node.js 2630. AWS EC2 is covered by the AWS BAA. The servers are optionally implemented in a multi-node cluster running behind AWS's high-availability load balancer. All communication with the webserver requires SSL encryption over HTTPS, and only traffic on HTTPS port is allowed in this embodiment. The load balancer is optionally configured with firewall and service to prevent denial of service attack (DDoS shield). Furthermore, all access is logged and stored in AWS CloudWatch. The disk storage for webservers are encrypted in this embodiment.

FHIR Server: The FHIR server 2640 is the main engine for integrating with various EHR systems in use by the patient's health care providers in this embodiment. An FHIR server itself is optionally implemented using AWS EC2 and secured much like the webserver. Each FHIR server in this embodiment includes an embedded XML database to facilitate the manipulation of XML data. No data in this embodiment will be stored after it is transformed. The disk storage for FHIR will be encrypted in this embodiment.

Support Servers and Services: The system in this embodiment has support servers that are only accessible from within the virtual private network. We optionally use AWS Key Management Service to manage encryption keys. System logs are optionally aggregated using AWS CloudWatch which is covered by AWS BAA. All logs in this embodiment are encrypted at rest and in flight. SNS notification services are also covered by AWS BAA; however, in the design of this embodiment the platform does not send any PHI over either SNS (push notification and SMS text message) or SES (email).

Mobile Application: The mobile applications 2650, 2660 are optionally built using React Native technology. Apple Watch and Android Wear applications are optionally implemented. For wearable devices, we write the applications in native iOS and Android code. The mobile applications run on any iPhone running iOS 8 or above and any Android device running Android operating system 5.0 and above. The applications in this embodiment logout automatically after a period of inactivity.

Web Application: In this embodiment, the web application 2670 is built using the React front-end framework. Use of this technology improves the componentization of the front end and thereby increases the flexibility of the display of records and other content.

Admin Website: The admin website 2680 in this embodiment is a dashboard built using React framework as well.

Logging Strategy: Logs are aggregated in this embodiment at two levels to meet HIPAA requirements—at the system level and at the application level. We optionally keep RDS general logs and EC2 access logs in AWS CloudWatch. The application level log in this embodiment keeps track of all user activity and is directly stored in S3 in encrypted form.

Additional Security Practice: The following security practice is optionally used to achieve the highest level of security. Access keys are kept securely and rotated periodically. Periodic vulnerability assessments are suggested for all web servers using AWS Inspector. All web servers in this embodiment can only be accessed by a very small number of people at a very small number of IP Addresses using 256-bit RSA keys.

Decentralized Open Ledger Medical Research Network

An exemplary decentralized open ledger medical research network has users who may play one or more of three roles, which, in some embodiments, include the following:

Researcher: Uses patient data to test hypotheses without knowing patient identities;

Practitioner: Has patient data including identifying information; and

Custodian: Keeps the system running by doing computational work, one designated custodian per release cycle.

One goal of the exemplary decentralized open ledger medical research network described herein is to completely anonymize patient records without relying on a single centralized point-of-trust. In some embodiments, this requires the following (with reference to FIGS. 21-24):

Patient identifying information 2105 is stripped from the treatment record before release as "de-identified treatment records";

Each patient is instead denoted by a unique identifier 2125 that is randomly generated from a large enough name space that there will always be at least tens of thousands as many possible names as the population of patients;

De-identified treatment records leave the treating physician or practitioner's control in encrypted form;

Release in decrypted only takes place after a sufficiently large number of records has been made available from multiple practitioners;

The decryption process does not allow a record to be traced back to the practitioner generating it. This includes protecting against an attacker who keeps track of the time at which each practitioner made a public (encrypted) release of data; and No one, including the custodian, can attach a record to the practitioner generating it, except for the practitioner itself. A breech of this security requires active cooperation of the custodian and a plurality of secret colluders among the practitioners who wish to break the security of a practitioner not in collusion.

The exemplary decentralized open ledger medical research network described herein relies, in some embodiments, on a public-key/private-key encryption system (using any of a number of available technologies and algorithms) that creates the following categories of key pairs 2220:

One key pair per individual practitioner; and

One common key pair per release cycle.

The release cycle for the exemplary decentralized open ledger medical research network described herein has a known start point, a number of interim record releases, and then a final verification/decryption phase. Described below are steps and functions performed at each of these phases.

At the start point of a release cycle, in some embodiments:

A group of practitioners 2210 is identified at the beginning of the cycle, and one of them is designated as custodian for the cycle 2215. A practitioner in the group may or may not contribute records during the cycle, but practitioners outside the group may not contribute until the next cycle;

The custodian establishes the count of participants (N) and a list establishing a fixed order for cycling through all participating practitioners minus the custodian (L, a list of N-1 names);

The custodian generates a private and public key pair for the cycle, denoted by κ in 2220, and The custodian securely sends the public key and the enumerated list to all participating practitioner by encrypting the public cycle key and the custodian list with the public key of each practitioner, so each practitioner gets a copy of the cycle public key by applying their private key.

During the release cycle, in some embodiments:

Every participating practitioner collects treatment records, which may be treatment records for existing patients and/or new patients, as well as demographic data for new patients (or, less often, for existing patients who change demographic category. On a daily or weekly basis within the release cycle, each practitioner does a dummy data dump as follows:

Patient identifying information is stripped out and replaced with a randomly generated unique identifier, or, where existing, with the unique identifier for that patient already in the research database from before;

Each identifier is appended to a random "salt" sequence and then encrypted with the practitioner's public key;

The remaining fields of the record are "confounded" by assigning random values that have no relation to the actual contents, but which cannot be distinguished from real record values. For example, if the patient received treatment "X" and had outcome "Y," then the released record will say "Treatment I and outcome J"; and The list of dummy records, with encrypted keys and confounding contents, are then privately sent to the custodian using the custodian's public key.

Subsequently, the custodian collects the dummy records from multiple practitioners until the number of records reach critical mass. At that point, the custodian initiates the last phase of the cycle.

In the final verification phase, in some embodiments:

The custodian randomizes the order of the dummy records so far received.

The custodian generates a list of compound keys (K, a list of length N-1) from the session private key and each practitioner's public key. These keys have two properties:

Data encrypted by them can be only be decrypted by someone who has both the public key for the session and the private key of the practitioner whose public key was used to make the compound key; and Having the public session key alone does not permit the identity of the practitioner whose public key was used to make the compound key;

(it is to be noted that any encryption scheme where key application is associative but not commutative would trivially generate such a compound key by applying the intended practitioner's public key to the private cycle key, (denoted in 2250 by 'hollow G' applied to 'solid kappa,' where hollow lettering stands for public keys and solid lettering for private keys), and the corresponding compound decryption key can be built by applying the practitioner's private key to the public session key, ('solid G' applied to 'hollow kappa'), thus ensuring that only practitioner G can decrypt by applying the compound decryption key (private key 'solid G' applied to public key 'hollow kappa') but no observer in possession of only the three public keys 'hollow G,' 'hollow kappa' and the composite key ('hollow G' applied to private key 'solid kappa') would know that it was practitioner G who holds the power to decrypt the message encrypted by the composite key).

A public hash value of the list of keys 2225 is created and sent privately to all participating practitioners. This allows any practitioner to detect future tampering with the list by a group of attackers which may include the custodian, as might happen if a compromised custodian aims to ensure that only compromised accomplices receive the packet after the target practitioner fills in their records.

The custodian picks (a) a number between 1 to N.

The randomly-ordered list of dummy records, the list of compound keys, and the number (a) are all appended into a single packet 2230 with a defined header, and encrypted with the key K(a) 2240. This means that only the practitioner whose key is (a) in the list of compound keys can decrypt it.

The packet is then encrypted with the public key 2250 of the first practitioner on the list and sent to that address.

The packet cycles around as follows:

A recipient decrypts the packet P0 with their private key to et P1.

The packet is then decrypted with the recipient's private compound key to yield P2.

If P2 does not have the defined header, then the recipient is not the one whose turn it is to add data, so P1 is encrypted with the public key of the next person on the cycle list.

If P2 does have the defined header then the practitioner takes the following steps:

1. Compare the list of compound keys to the hash to make sure it has not been tampered with since the phase began.
2. For each record, apply the private key to the record identifier. If the decrypted id belongs to the practitioner, then overwrite the dummy record with the real unencrypted ID and the real unconfounded data.
3. Possible precaution: if any record has an ID that does not yield to the decryption, but which accidentally is identical to a patient record that the practitioner just generated for a new patient, then let the unknown other practitioner keep that ID and generate a fresh ID for that patient.
4. Re-order all records randomly. This will include the practitioners own freshly corrected records, dummy records from practitioners who have not had a turn yet, and real records from practitioners who had gone through this step before.
5. Picks a number (b) from 1 to N-1, excluding the numbers already in the packet from before (i.e., (a) the first time around, (a,b) the second etc.)
6. If a number (b) is found, then append (b) to the list of numbers 2330, and use the compound key K(b) to encrypt the new packet P3 2340, consisting of the freshly shuffled records, the same old list of compound keys, the list of numbers including the new one (b). The encryption with the compound key will yield packet P4.
7. Encrypt P4 with the public key of the practitioner 2350 who is next on the cycle list and send it there.

8. If all numbers from 1 to N-1 are already in the list, then it is time to send a new packet Q1 2430, consisting only of the randomized list of records, to the custodian, by applying the custodian's private key to the packet Q1 yielding Q2 2440.

9. As a final precaution against tampering, the practitioner who can no longer find an unused number from 1 to N-1 announces the impending end of the cycle to all other practitioners participating in the cycle, and each of them (except the custodian) confirms that they have had exactly one turn being able to decrypt the circulated message.

After the packet has completed N-1 rounds of each of the N-1 non-custodial participants, and each affirms that they were able to decrypt the packet exactly once, the packet goes to the custodian as described in item 5 above. Since the custodian is also a practitioner, the custodian then corrects the records that belong to their organization as in item 2 above.

All other records in the packet will have already been corrected, but no participant at any stage was even able to guess which other practitioner added which records.

The list of records is then released to researchers.

Accordingly, the exemplary decentralized open ledger medical research network described herein provides an anonymization scheme, which a doctor needs to follow after de-identifying the patient record before releasing it for use by researchers. The scheme prevents an attacker posing as another doctor in the same network from guessing which patient came from each doctor, since knowing that could make it easier to guess that, for example, patient identified by a random identifier is actually a particular individual because only one patient of a particular doctor had a specific medical history.

If the patient is allowed to know the random identifier assigned to her, then the system can allow the patient to search for research that was generated using in part some of that patient's data. A different encryption scheme, to be invented, or a trust-based system where a trusted party is allowed to know the relationship between each member of a class of patients and that patient's random identifier, would need to be put in place if it is desired to have the patients receive some revenue stream based on any lucrative use of their data.

Figure 28:
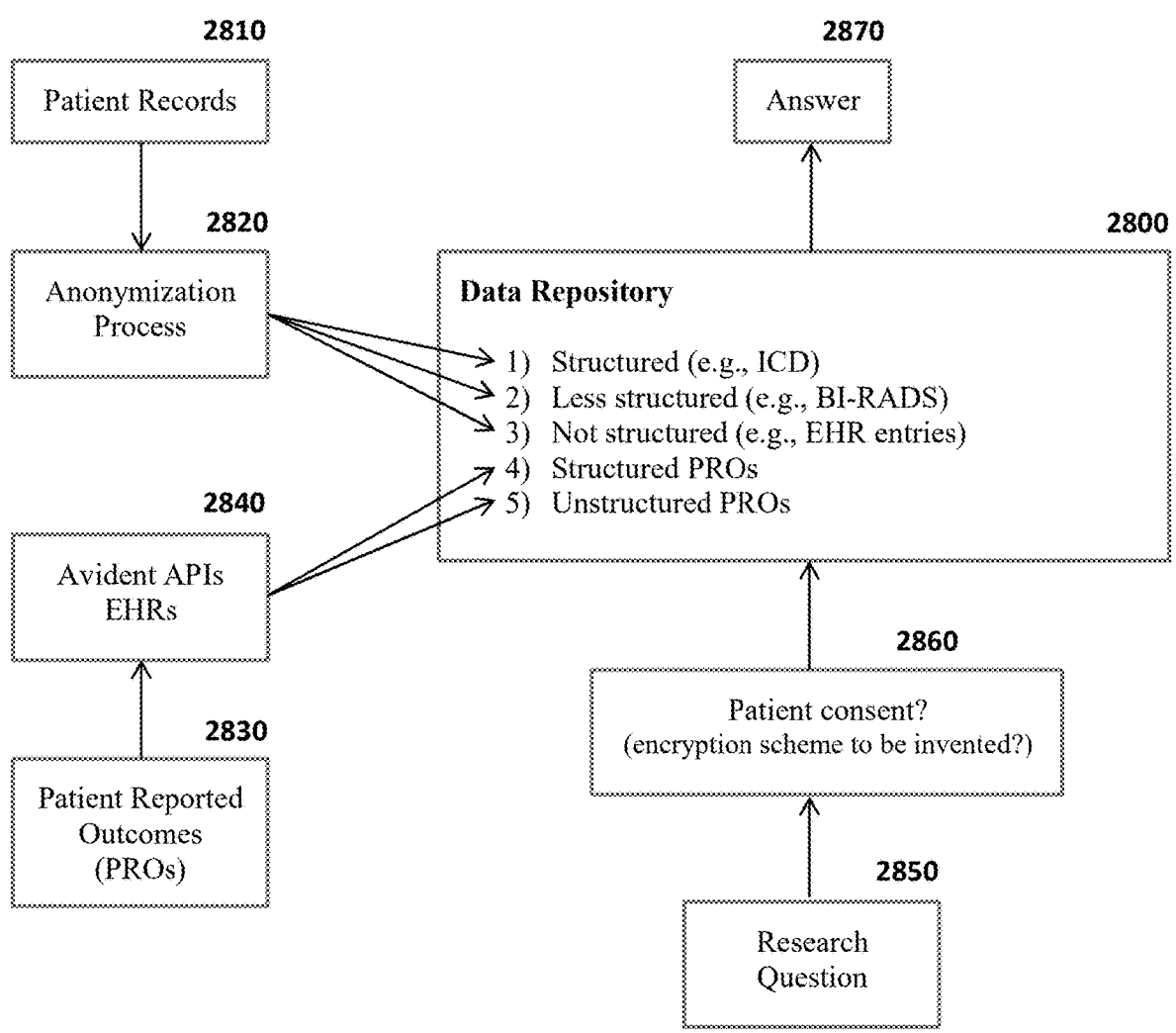
FIG. 28 is a schematic diagram illustrating an exemplary data repository including anonymization features allowing researcher to pose questions while allowing patients to "own" their data.

FIG. 28 illustrates an exemplary "big picture" view for a real-world data repository 2800 that serves to accelerate innovation and creates a resource of CQI for medical decision making. Such a data repository de-formalizes the research process. Every patient and encounter can be a research subject with consent and the patient "owns" their own data. In this example, patient records 2810 are subjected to an anonymization process 2820 before being introduced to the data repository 2800 and stored, for example, as structured data (for example International Classification of Diseases (ICD) data), less structured data (for example Breast Imaging-Reporting and Data System (BI-RADS) data), and unstructured data (for example EHR entries). Further in this example, patient reported outcome (PRO) data 2830 are fed into APIs and EHRs 2840 and introduced to the data repository 2800 and stored as, for example, structured PROs and unstructured PROs. The described data repository 2800 allows researchers to pose research questions 2850 including deanonymization and patient consent parameters 2860 against the data in the repository 2800 to generate research question answers 2870.

Digital Processing Device

In some embodiments, the platforms, systems, media, and methods described herein include a digital processing device, or use of the same. In further embodiments, the digital processing device includes one or more hardware central processing units (CPUs) or general-purpose graphics processing units (GPGPUs) or quantum processing units (QPUs) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, handheld computers, Internet appliances, mobile smartphones, tablet computers, personal digital assistants, video game consoles, and voice-service devices such as Amazon Alexa®, Google Home® or Apple Siri® speakers. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, flash memory devices, magnetic disk drives, solid-state disk drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In still further embodiments, the input device is a combination of devices such as those disclosed herein.

Figure 27:
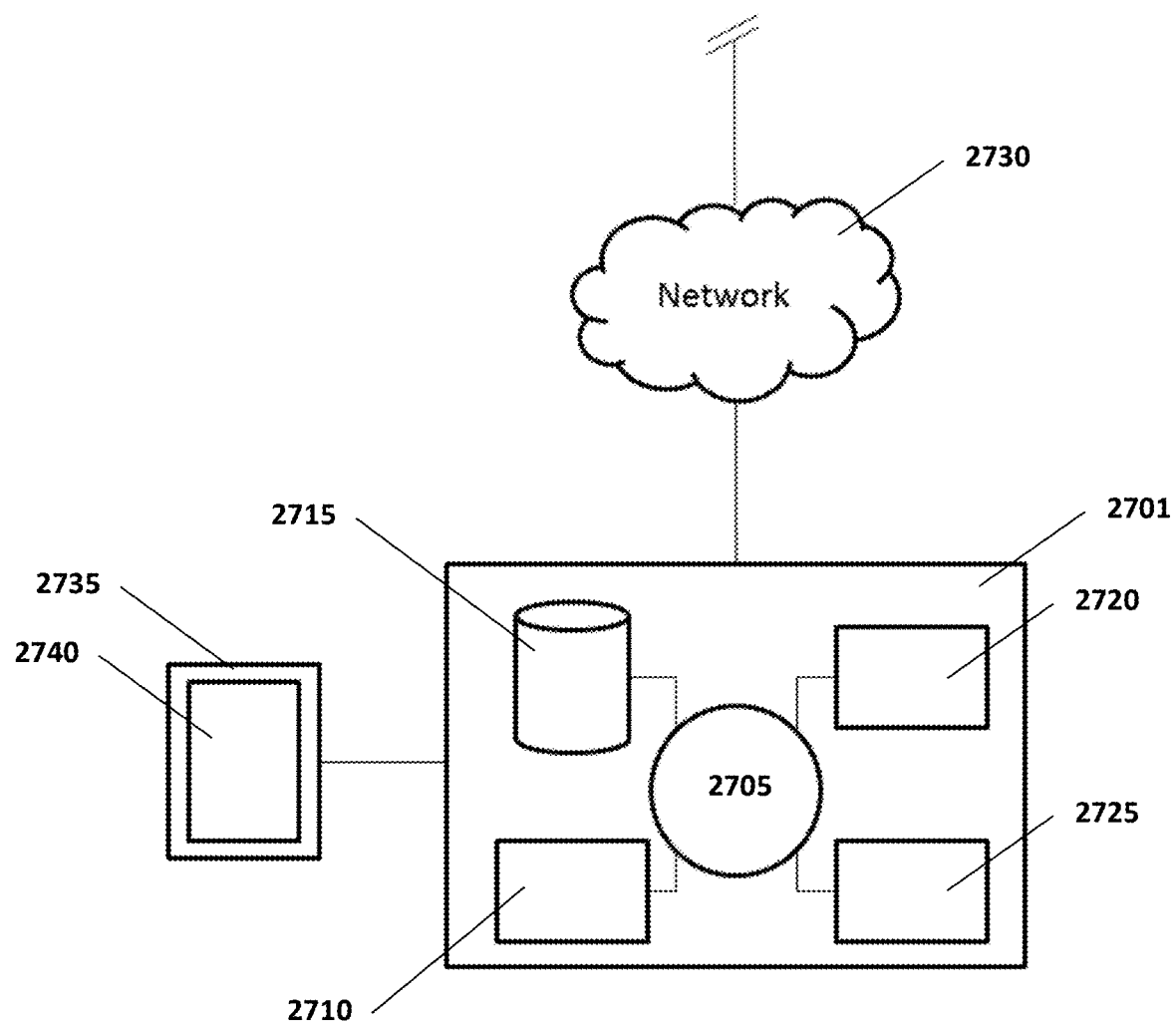
FIG. 27 is a block diagram illustrating an exemplary digital processing device such as a mobile device or a personal computer; in this case, a digital processing device with one or more CPUs, memory, a communication interface, and a display.

Referring to FIG. 27, in a particular embodiment, an exemplary digital processing device 2701 is programmed or otherwise configured to participate in the platforms and/or systems described herein, execute the applications described herein, host the media described herein, and/or perform the methods described herein. In this embodiment, the digital processing device 2701 includes a central processing unit (CPU, also "processor" and "computer processor" herein) 2705, which can be a single core or multi core processor, or a plurality of processors for parallel processing. The digital processing device 2701 also includes memory or memory location 2710 (e.g., random-access memory, read-only memory, flash memory, etc.), electronic storage unit 2715 (e.g., hard disk), communication interface 2420 (e.g., network adapter) for communicating with one or more other systems, and peripheral devices 2425, such as cache, other memory, data storage, and/or electronic display adapters. The memory 2710, storage unit 2715, interface 2720, and peripheral devices 2725 are optionally in communication with the CPU 2705 through a communication bus (solid lines), such as a motherboard. The storage unit 2715 can be a data storage unit (or data repository) for storing data. The digital processing device 2701 is, in some cases, operatively coupled to a computer network ("network") 2730 with the aid of the communication interface 2720. In various embodiments, the network 2730 is the Internet, an intranet and/or extranet, or an intranet and/or extranet that is in communication with the Internet. The network 2730 in some cases is a telecommunication and/or data network. The network 2730, in some cases, includes one or more computer servers, which can enable distributed computing, such as cloud computing. The network 2730, in some cases, with the aid of the device 2701, can implement a peer-to-peer network, which may enable devices coupled to the device 2701 to behave as a client or a server.

Continuing to refer to FIG. 27, the CPU 2705 is configured to execute a sequence of machine-readable instructions, which can be embodied in a program or software. The instructions are optionally stored in a memory location, such as the memory 2710. The instructions are, in some cases, directed to the CPU 2705, which can subsequently program or otherwise configure the CPU 2705 to implement methods of the present disclosure. Examples of operations performed by the CPU 2705 include fetch, decode, execute, and write back. The storage unit 2715 optionally stores files, such as drivers, libraries and saved programs. In some cases, the storage unit 2715 stores user data, e.g., user preferences and user programs. The digital processing device 2701, in some cases, includes one or more additional data storage units that are external, such as located on a remote server that is in communication through an intranet or the Internet. Also, the digital processing device 2701 communicates, in some cases, with one or more remote computer systems through the network 2730.

Non-Transitory Computer Readable Storage Medium

In some embodiments, the platforms, systems, media, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft®.NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous JavaScript and XML (AJAX), Flash® ActionScript, JavaScript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, JavaScript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome WebStore, BlackBerry® App World, App Store for Palm devices, App Catalog for webOS, Windows® Marketplace for Mobile, Ovi Store for Nokia® devices, Samsung® Apps, and Nintendo® DSi Shop.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

In some embodiments, quantum computing hardware or architectures may be substituted, and specialized software paradigms may be used in implementing software to run on such hardware or architectures, with the goal of supplying more efficient or more secure versions of modules of the present invention, including but not limited to the public-key/private-key encryption and decryption component of the anonymization module.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A platform comprising:
   a) a server processor configured to provide a web-based data store comprising:
      i) a software module interfacing with a plurality of electronic medical records; and
      ii) a structured data store comprising a plurality of patient profiles, each patient profile comprising aggregated electronic medical records;
   b) a mobile processor configured to provide a mobile clinician application comprising:
      i) a software module presenting a group management interface allowing a project lead to define and edit a clinical project comprising: a patient profile and a plurality of clinicians including a treating physician;
      ii) a software module providing an interdisciplinary collaboration environment comprising: a clinician-facing messaging service, a document sharing service, a list of performed and upcoming clinical procedures, and a notification service for the plurality of clinicians and pertaining to the clinical project; and
      iii) a software module performing clinician engagement analytics;

c) the server processor configured to provide a web-based patient portal comprising a software module providing a patient help center comprising: a patient-facing messaging service, the list of performed and upcoming clinical procedures, and a notification service for the patient and pertaining to the clinical project; and d) the server processor configured to provide an aggregated relevant decision driving engine comprising:
   i) a translation module configured to express the aggregated electronic medical records in a format that is human-readable and accessible to a native inference engine, a supervised machine learning algorithm, or both;
   ii) a notation module configured to express relationships between treatment steps to generate human-readable and human-editable node-and-arc diagrams and to transmit the diagrams as readable instructions to the native inference engine or the supervised machine learning algorithm;
   iii) an anonymization module configured to maintain separation between patient treatment or demographic records and private patient information comprising the identity of individual patients or of their treating physician, without implicitly or explicitly relying on trust in any party subject to attack by a malicious actor seeking such access, wherein the anonymization module utilizes a zero-trust-architecture distributed ledger system, via a circular queue, configured to apply an arbitrary number of cycles of decryption, authentication, encryption, and inalterable electronic tagging of incoming and outgoing packets of data based on identities of parties requesting to read or write data according to permissions assigned to each party;
   iv) the native inference engine configured to receive inputs from the translated medical records of a patient and a subset of interlinked treatment steps selected by the treating physician to generate outputs comprising predictions and probabilities; and
   v) the supervised machine learning algorithm configured to read and aggregate the translated medical records of multiple patients and combine them with one or more tumor registries to test hypotheses about the efficacy of potential courses of treatment for particular subsets pf patients.

2. The platform of claim 1, wherein one or more of the inference engine inputs are parsed from the translated medical records and comprise a provider decision or a patient behavior.

3. The platform of claim 1, wherein one or more of the inference engine outputs comprise a result of a diagnostic procedure or the patient's response to a treatment.

4. The platform of claim 1, wherein the clinical project comprises diagnosis and treatment of disease.

5. The platform of claim 4, wherein the disease comprises cancer.

6. The platform of claim 5, wherein the cancer comprises breast cancer.

7. The platform of claim 1, wherein the zero-trust-architecture distributed ledger system utilizes a permissioned Blockchain, Merkle Tree, or other public-private key encryption models, including Quantum-based encryption schemes.

8. The platform of claim 7, wherein the party requesting to read or write data is a medical researcher testing one or more hypotheses about patient treatment.

9. The platform of claim 7, wherein the party requesting to read or write data is a medical practitioner seeking latest available data about the efficacy of a certain treatment for an existing patient.

10. The platform of claim 7, wherein the party requesting to read or write data is a patient or patient-authorized agent seeking detailed understanding of past treatment steps, or past or present descriptions of the patient's condition, or potential future treatment steps and probabilities associated with the different outcomes of each treatment option, including any physician's comments on any of the above.

11. The platform of claim 7, wherein the distributed ledger system is used to plan, initiate, conduct, track, or report a clinical trial in an accelerated fashion.

12. The platform of claim 7, wherein the native inference engine is programmed to notify one or more of the plurality of clinicians to one or more clinical trials relevant to the patient using the notification service of the interdisciplinary collaboration environment.

13. The platform of claim 1, wherein the mobile clinician application is a native mobile application.

14. The platform of claim 1, wherein the clinician-facing messaging service of the interdisciplinary collaboration environment allows a clinician to send and receive text messages, voice messages, photo messages, video messages, or any combination thereof.

15. The platform of claim 1, wherein the clinician-facing messaging service of the interdisciplinary collaboration environment allows a clinician to send a message to: the patient, the plurality of clinicians, or a subset of the plurality of clinicians.

16. The platform of claim 1, wherein the clinician-facing messaging service of the interdisciplinary collaboration environment allows a clinician to poll the plurality of clinicians or a subset of the plurality of clinicians.

17. The platform of claim 1, wherein the notification service of the interdisciplinary collaboration environment utilizes SMS, push notification, email, voice mail, or any combination thereof.

18. The platform of claim 1, wherein the document sharing service of the interdisciplinary collaboration environment allows sharing of lab results, pathology reports, medical images, radiology reports, surgical reports, or any combination thereof.

19. The platform of claim 1, wherein the patient-facing messaging service of the patient help center allows the patient to send and receive text messages, voice messages, photo messages, video messages, or any combination thereof.

20. The platform of claim 1, wherein the patient-facing messaging service of the patient help center allows the patient to send a message to: the plurality of clinicians or a subset of the plurality of clinicians.

21. The platform of claim 1, wherein the notification service of the patient help center utilizes SMS, push notification, email, voice mail, or any combination thereof.

22. The platform of claim 1, wherein the server processor is further configured to provide a clinical analytics system comprising a software module checking the performed and upcoming clinical procedures against a predetermined standard and generating a notification if any procedure is outside the standard.

23. The platform of claim 1, wherein the server processor is further configured to provide a web-based administrative dashboard application comprising a software module generating a suite of administrative reports.

24. The platform of claim 23, wherein the suite of administrative reports comprises one or more of: a quality of patient care report, a cost of patient care report, a patient profile report, an upcoming procedure report, a rate of guideline compliance report, and a clinician engagement report.

* * * * *